US007939110B2

(12) United States Patent
Wu

(10) Patent No.: US 7,939,110 B2
(45) Date of Patent: May 10, 2011

(54) COMPOSITION AND METHOD FOR TREATING AUTOIMMUNE DISEASE AND MUCOSAL DISORDER

(75) Inventor: Rong-Tsun Wu, Taipei (TW)

(73) Assignee: National Yang-Ming University, Taipei (TW)

( * ) Notice: Subject to any disclaimer, the term of this patent is extended or adjusted under 35 U.S.C. 154(b) by 588 days.

(21) Appl. No.: 11/899,590

(22) Filed: Sep. 5, 2007

(65) Prior Publication Data

US 2009/0099128 A1 Apr. 16, 2009

Related U.S. Application Data

(62) Division of application No. 11/121,721, filed on May 4, 2005, now abandoned.

(51) Int. Cl.
*A61K 36/00* (2006.01)
(52) U.S. Cl. ........................................................ 424/725
(58) Field of Classification Search .......................... None
See application file for complete search history.

(56) References Cited

OTHER PUBLICATIONS

Chen et al. "Hypoglycemic effect of the polysaccharide from Dendrobium moniiforme (L.) Sw." Journal of Zhejiang University (Science Edition)), vol. 30, No. 6 (2003) 693-696, Abstract only.*
Castagna et al.. "Anterior uveitis and diabetes mellitus: immunological study", Opthalmologica, vol. 209, No. 2 (1995) 53-55, Abstract only.*
Weiner, Howard L., M.D., "Oral Tolerance for the Immune Treatment of Autoimmune Diseases", Annu. Rev. Med. 48:341-351 (1997).
Whitacre, C.C., et al., "Oral Tolerance in Experimental Autoimmune Encephalomyelitis", Annals of the New York Academy of Sciences, 778(1):217-227 (1996).
Kernéis, Sophie, et al., "Conversion by Peyer's Patch Lymphocytes of Human Enterocytes Into M Cells That Transport Bacteria", Science 277:949:952 (1997).
Madara, James L., "The Chameleon Within: Improving Antigen Delivery", Science 277:910-911 (1997).
MacDonald, Thomas W. and Giovanni Monteleone, "IL-12 and Th1 Immune Responses in Human Peyer's Patches",Trends Immunol. 22(5):244-247 (2001).
Weiner, Howard L., "Oral Tolerance, An Active Immunologic Process Mediated by Multiple Mechanisms", J. Clin. Invest. 106(8):9350937 (2000).
Weiner, Howard L., "Oral Tolerance: Immune Mechanisms and Treatment of Autoimmune Diseases", Immunol. Today 18:335-343 (1997).
Booth, Catherine and Christopher S. Potten, "Gut Instincts: Thoughts on Intestinal Epithelial Stem Cells", J. Clin. Invest. 105:1493-1499(2000).

van den Brink, Gijs R., et al., "Epithelial Cell Differentiation-A Mather of Choice", Science 294:2115-216 (2001).
Hershberg, Robert M. and Lloyd F. Mayer, "Antigen Processing and Presentation by Intestinal Epithelial Cells-Polarity and Complexity", Immunol. Today 21:123-128 (2000).
Van De Wal, Yvonne, et al., "Delineation of a CD1d-Restricted Antigen Presentation Pathway Associated With Human and Mouse Intestinal Epithelial Cells",Gastroenterology 124:1420-1431(2003).
Ganz, Tomas, "Defensins: Antimicrobial Peptides of Innate Immunity", Nat. Rev. Immunol. 3:710-720 (2003).
Hooper, Lora V., et al., "Angiogenins: A New Class of Microbial Proteins Involved in Innate Immunity", Nat. Immunol. 4(3):269-273 (2003).
Medzhitov, Ruslan and Charles A. Janeway, Jr., "Innate Immunity: The Virtues of a Nonclonal System of Recognition", Cell 91: 295-298(1997).
Underhill, David M. and Adrian Ozinsky, "Toll-like Receptors: Key Mediators of Microbe Detection", Curr. Opin. Immunol. 14:103-110 (2002).
Khimich, Darina, et al., "Hair Cell Synaptic Ribbons Are Essential for Synchronous Auditory Signalling", Nature 433:889-894 (2005).
Lund, Jennifer M., et al., "Recognition of Single-Stranded RNA Viruses by Toll-Like Receptor 7", Proc. Natl. Acad. Sci. U.S.A. 101(15):5598-5603 (2004).
Cario, Elke and Daniel K. Podolsky, "Differential Alteration in Intestinal Epithelial Cell Expression of Toll-Lke Receptor 3 (TLR3) and TLR4 in Inflammatory Bowel Disease", Infection and Immunity 68:7010-7017 (2000).
Akhtar, Mahmood, et al, "Bacterial DNA Evodes Epithelial IL-8 Production by a MAPK-Dependent, NF-•B-Independent Pathway", FASEB J. 17:1319-1321 (2003).
Rakoff-Nahoum, Seth, et al. "Recognition of Commensal Microflora by Toll-Like Receptors Is Required for Intestinal Homeostasis", Cell 118:229-241 (2004).
Mizushima, Yukio, et al., "Oral Administration of Leflunomide (HWA486) Results in Prominent Suppression of Immunoglobulin E Formation in a Rat Type 1 Allergy Model", The Journal of Pharmacology and Experimental Therapeutics 288:849-857 (1999).
Flores-Paz, Rocio, et al., "Etiologia de la Infeccion Cervico Vaginal en Pacientes del Hospital Juarez de Mexico", Salud Publica Mex, vol. 45 Suppl. 5, pp. S694-S697 (2003), Abstract.
Avichezer, Dody, et al., "Identification of a New Epitope of Human IRBP that Induces Autoimmune Uveoretinitis in Mice of the H-2$^{b}$I Haplotype", nvestigative Ophthalmology & Visual Science 41(1):127:131 (2000).

* cited by examiner

*Primary Examiner* — Amy L Clark
(74) *Attorney, Agent, or Firm* — Volpe and Koenig, P.C.

(57) ABSTRACT

The present invention provides the composition and the method for treating autoimmune diseases and a mucosal disorder via oral-tolerance induction and innate immunity promotion. The composition for treating the autoimmune disease and mucosal disorder includes the polysaccharide prepared from a plant, wherein the plant belongs to Genus *Dendrobium*.

2 Claims, 22 Drawing Sheets
(5 of 22 Drawing Sheet(s) Filed in Color)

COMPOSITION AND METHOD FOR TREATING AUTOIMMUNE DISEASE AND MUCOSAL DISORDER

CROSS REFERENCE TO RELATED APPLICATIONS

This application is a divisional application of U.S. application Ser. No. 11/121,721, which was filed on May 4, 2005 and is incorporated by reference herein as if fully set forth.

FIELD OF THE INVENTION

This invention relates to a composition and a method for treating autoimmune disease and mucosal disorder, and more particularly to a composition including polysaccharides derived from *Dendrobium* and a method including the administration of polysaccharides derived from *Dendrobium* for treating autoimmune disease and mucosal disorder via oral tolerance induction and innate immunity promotion.

BACKGROUND OF THE INVENTION

A basic property of the immune system is the immunologic tolerance that provides for self/non-self discrimination, so that the immune system can protect the host from external pathogens without reacting against itself. When the immune system reacts against itself, autoimmune disease results. (*Annu. Rev. Med.* 48:341-351, 1997)

Oral tolerance has been proven to be of therapeutic benefit in autoimmune diseases, including uveitis, collagen-induced arthritis, adjuvant arthritis, systemic lupus erythematosus, multiple sclerosis, thyroiditis, myasthenia gravis, inflammatory bowel disease and diabetes. (*Annals of the New York Academy of Scien. ces* 778(1): 217-227, 1996)

An orally administered antigen encounters the gut-associated lymphoid tissue (GALT), which is a well-developed immune network. The GALT consists of villi, lamina propria, intraepithelial lymphocytes and Peyer's patch, wherein Peyer's patch consists of lymphoid nodules interspersed among the villi. The epithelium that lines the gut contains M cells for transporting antigens and microorganisms. Antigens and pathogens in the gut can only penetrate the barrier through M cells, specialized to deliver antigen directly to underlying immune cells. Then, the intraepithelial lymphocytes recognizing the antigens translocate to Peyer's patches to trigger immune responses. In Peyer's patches, B cells and macrophages present the antigens to lymphocytes, and then the antigen-specific lymphocytes circulate to the lamina propria in the mucosal system (such as mucosal surface of respiratory tract) of the body. However, M cells are scattered and few, less than 0.1% of epithelial cells. (*Science* 277:949952, 1997; *Science* 277:910-911, 1997)

The intestinal immune system includes innate immunity and adaptive immunity for protecting against diseases mediated via oral administration. The portion of tissue infected by pathogens secretes chemokines for inducing the non-specific innate immune responses of macrophages, monocytes, granulocytes and natural killer cells. Macrophages and granulocytes can directly take pathogens by phagocytosis. Natural killer cells are the immune cells in the body that first respond to viral infections or cells infected by other pathogens. Natural killer cells not only attack the target cells, but also secrete cytokines for regulating immune responses such as interferon-gamma (IFN-γ), transforming growth factor-beta (TGF-β), tumor necrosis factor-alpha (TNF-α), interleukin-5 (IL-5) and interleukin-10 (IL-10). Macrophages and other antigen presenting cells, such as dendritic cells, present antigens to T cells via MHC class II molecules and co-stimulators on the cell surface, so as to further activate immune responses, i.e. cell-mediated immunity and humoral immunity respectively performed by T cells and B cells. Mucosal immunity is mainly regulated by cytokines secreted from $CD4^+$ T cells. Interleukin-4 (IL-4), IL-5, interleukin-6 (IL-6) and IL-10 secreted from type 2 helper T (TH2) cells involve in stimulating B cells for antibody production. TGF-β secreted from type 3 helper T (TH3) cells induces B cells to produce IgA. (*Trends Immunol.* 22:244-247, 2004; *J. Clin. Invest.* 106:935-937, 2000)

Mucosal immune responses are not only induced in the gut, but also in the mucosal system of the whole body. Once there are antigen-specific lymphocytes activated in the inductive site-Peyer's patch in intestine, lymphocytes travel through lymph drain and blood to effector sites, including lamina propria and rectum, genital tract, lung and so on. Then, the antibodies are produced and can be detected at these effector sites. This homing phenomenon is called the common mucosal immune system. Due to the common mucosal immune response, the antibodies induced by oral administration are distributed in the whole body. If the antigen is delivered via oral administration, systematic tolerance or IgA, i.e. oral tolerance, is induced. Oral tolerance includes both systematic unresponsiveness and mucosal responsiveness, wherein the former prevents the whole body from autoimmune diseases, and the later induces active suppression of a specific antigen. Therefore, the mucosal immune system tends to inhibit inflammatory immune responses and further enhance the presentation of IgA in the non-inflammatory local mucosa. (*Immunol. Today* 18:335-343, 1997)

The surface of the gastrointestinal tract is lined by a simple columnar epithelium to form a barrier against the excessive absorption of bacteria, food antigens and large molecules, and moreover the transportation of small molecules is controlled by the tight junction formed in the barrier. The crypts embedded in the connective tissue include stem cells for regenerating the intestinal epithelial cells. In addition to the intestinal epithelia cells, the intestinal stem cells also can differentiate into Goblet cells and enteroendocrine cells for secreting mucin, and into Paneth cells for secreting antimicrobial peptides. In addition to the Paneth cells staying in the stem cells region, the differentiated cells migrate to the top of the villi. (*J. Clin. Invest.* 105:14931499, 2000; *Science* 294: 2115-2116, 2001)

It is a reasonable suggestion that the intestinal epithelia cells play a critical role for influencing immune responses to various antigens in the intestinal lumen due to the special location of the epithelial cells. The intestinal epithelial cells can express antigen-presenting molecules as antigen-presenting cells (APCs) so as to regulate T-cell responses in the intestinal mucosa. (*Immunol. Today* 21:123-128, 2000) Antigen presenting molecules expressed by the intestinal epithelial cells include MHC class I, MHC class II and CD1d. (*Gastroenterology* 124:1420-1431, 2003) The MHC class I and MHC class II are expressed on the basolateral membrane of epithelial cells, wherein MHC class I is responsible for coupling with CD8+ cells, and MHC class II is responsible for coupling with CD4+ cells. CD1d activates NK T cells via glycolipid. The intestinal epithelial cells play a critical role in the mucosal immune system.

In addition to being the physical barrier, the intestinal epithelial cells secrete antimicrobial peptides against microbes in the gastrointestinal tract and provide signals to other cells. (*Immunol. Today* 21:123-128, 2000; *J. Clin. Invest.* 95:55-65, 1995) There are specific antimicrobial peptides, defensins. Defensins are 3-5 kD proteins, which include the α-defensin and β-defensin family, which has 8 peptides. These defensins have organ-specific expression patterns in the epithelial cells of oral mucosa, lung and gastrointestinal tract. (*Eur. J. Gastroenterol. Hepatol.* 13:771-776, 2001; *Nat. Rev. Immunol.* 3:710-720, 2003) When the gastrointestinal tract is infected, the intestinal epithelial cells express defensins, the defensins function as chemokines to induce NK cells and dendritic cells to the infected areas, and to perform the so-called innate immunity. In addition to the induction of innate immunity, defensins induce the dendritic cells to express co-stimulator (B7.2) through the toll-like receptor 4, so as to induce the proliferation of T cells. Therefore, defensins involve the link between innate immunity and adaptive immunity.

Other antimicrobial proteins, angiogenins, were considered to involve the angiogenesis of cancer cells; however, in 2003, Hooper disclosed that angiogenins are produced by the Paneth cells in the gastrointestinal tract under normal physiological conditions, and stored in the cellular granules. The angiogenins are secreted into the gastrointestinal tract in response to the lipopolysaccharide stimulation. Comparing the Germ free mice and the mice colonized with intestinal bacteria, it is found that angiogenins are significantly increased due to the presence of the intestinal bacteria. Like defensins, the angiogenins are bactericidal and modulated by local environmental conditions encountered at infected sites. (*Nat. Immunol.* 4:269-273, 2003)

In addition to secreting antimicrobial peptides against pathogen infection, the intestinal epithelial cells produce many signals for regulating the immune responses in the gastrointestinal tract. In order to protect the host by destroying invading microbes, the intestinal epithelial cells should immediately respond to the invading microbes via the defense mechanism. The defense mechanism is known as the innate immunity system, which uses germline-encoded pattern-recognition receptors for the recognition of the macromolecules of the microbial pathogens, such as lipopolysaccharide present in the cell wall of Gram-negative bacteria. In recent years, the manner in which receptors activate cells has been disclosed. In adult *Drosophila*, it is shown that Toll induces antifungal and antibacterial peptides upon infection. Medzhitov and Janeways et al. disclose that in mammals, the activation of Tolllike receptor (TLR) results in induction of cytokines and costimulatory molecules required for the activation of the adaptive immune response. (*Cell* 91:295-298, 1997) The intracellular signaling pathways activated by TLRs share much in common with IL-1R signaling due to their conserved TIR (Toll/IL-1R homology) domains. When the endotoxin is recognized by TLRs, nuclear translocation of NF-kB is triggered to regulate the transcriptions of other genes involved in immune responses. Subsequently, the proinflammatory cytokine genes are activated, antimicrobial peptides are secreted, and the chemokines, such as IL-8, MIP and MCP-1, are secreted. The macrophages and NK cells are induced by these chemokines so as to translocate to the infected site and to destroy the infected cells. (*Cell* 91:295-298, 1997; *Curr. Opin. Immunol.* 14:103-110, 2002) Hence, toll-like receptors not only induce the innate immunity system, but also indirectly induce the adaptive immunity system due to the secretion of proinflammatory cytokines triggered by NF-kB activation.

In human cells, there are at least 10 different TLRs, wherein TLR-2, TLR-4 and TLR-9 are more characterized members of the TLR family. TLRs have been shown to mediate the recognition of many types of pathogens, including bacteria and viruses. TLR-4 is the receptor for Gram-negative bacterial LPS, TLR-2 is the receptor for Gram-positive bacterial peptidoglycan, and TLR-9 is the receptor for the unmethylated and phosphorylated cytosine-guanine oligonucleotide, CpG. (*Curr. Opin. Immunol.* 14:103-110, 2002) TLR3 can recognize double strand RNA virus, (*Nature* 433:887-892, 2005) and TLR7 can recognize single strand RNA virus. (*Proc Natl Acad Sci USA.* 101(15):55985603, 2004) When TLR signal pathway is activated, the innate immunity or antiviral response can be induced for host protection.

In normal intestinal epithelial cells, TLR-3 and TLR-5 are constitutively expressed, while TLR2 and TLR4 are barely detectable. (*Infection and Immunity* 68:7010-7017, 2000) IL-8 is produced by the epithelial cells in response to the stimulation of the bacterial DNA. (*FASEB J.* 17:1319-1321, 2003) In intestinal epithelial cells, the bacterial CpG oligonucleotides are the ligands for the TLR-9. Furthermore, the intestinal epithelial cells do not induce inflammation in response to all foreign substances, i.e. the intestinal epithelial cells tolerate commensal microflora, while the intestinal epithelial cells provide danger signals to APCs under potential pathogenic conditions or autoimmune diseases, so as to induce the inflammation formed by T cells mediated by APCs. (*Cell* 118:229-241, 2004)

Under normal steady-state conditions, recognition of commensal bacteria by TLRs plays a crucial role in protection against gut injury. (*Cell* 118: 229-241, 2004) But in human inflammatory bowel disease (IBD), a Th1-mediated pathological effect is thought to be due to aberrant mucosal immune response to the microflora. (*Gastroenterol. Clin. North Am.* 31: 41-62, 2002) These findings reveal that TLRs control mucosal homeostasis between host—commensal.

It is well-known that oral administration of a Chinese herbal extract regulates the development of the immunity. It is very possible the Chinese herbal extract regulates the development of the immunity via the intestinal mucosal immunity. *Dendrobium* species is considered to be the most precious Chinese herb. A *Dendrobium* species belongs to an orchid family, and its stem is the mainmedicinal part of the plant. It tastes a little sweet and brackish. Some Chinese medical codices disclose that the *Dendrobium* species as the curative for some illnesses such as mucosal disorders, stomach disorders and ophthalmic disorders. According to our previous research experience, it appears that *Dendrobii Herba* is the most curative medicinal species.

SUMMARY OF THE INVENTION

The present invention provides a method for preparing the polysaccharide derived from *Dendrobium* and further provides the pharmaceutical use of the polysaccharide derived from *Dendrobium*.

It is an aspect of the present invention to provide a method for preparing a polysaccharide from a plant. The method includes the steps of a) extracting the plant with a first alcohol to obtain a first extract, b) extracting the remaining material after step a) with a solvent to obtain a second extract, and c) precipitating the second extract with a second alcohol to obtain the polysaccharide.

Preferably, the plant belongs to the Genus *Dendrobium*.
Preferably, the first alcohol is a methanol.
Preferably the solvent is water.
Preferably, the second alcohol is an ethanol.
In accordance with the present invention, after extracting the remaining material after step a) with the solvent in the step b), the method further includes steps of centrifuging and filtering so as to obtain the second extract.

It is another aspect of the present invention to provide a composition for treating an autoimmune disease and mucosal disorder. The composition includes a polysaccharide prepared from a plant, wherein the plant belongs to *Dendrobium*, and an antigen associated with induction of an autoimmune disease.

Preferably, the polysaccharide is prepared by the method provided in the present invention.

In accordance with the present invention, the autoimmune disease can be uveitis.

It is another aspect of the present invention to provide a method for treating an autoimmune disease and mucosal disorder in a mammal. The method includes a step of administrating an antigen and a polysaccharide to the mammal, wherein the antigen is associated with induction of an autoimmune disease, and the polysaccharide is prepared from a plant belonging to the Genus *Dendrobium*.

In accordance with present invention, the administration of the polysaccharide can be performed in a manner of an oral administration.

In accordance with the present invention, the autoimmune disease can be uveitis.

It is another aspect of the present invention to provide a composition for treating an autoimmune disease and mucosal disorder. The composition includes a polysaccharide prepared from a plant, wherein the plant belongs to the Genus *Dendrobium*.

In accordance with the present invention, the autoimmune disease can be uveitis.

It is another aspect of the present invention to provide a method for treating an autoimmune disease and mucosal disorder in a mammal. The method includes a step of administrating a polysaccharide to the mammal, wherein the polysaccharide is prepared from a plant belonging to the Genus *Dendrobium*.

In accordance with the present invention, the administration of the polysaccharide is performed in a manner of an oral administration.

In accordance with the present invention, the autoimmune disease can be uveitis.

The above aspects and advantages of the present invention will become more readily apparent to those ordinarily skilled in the art after reviewing the following detailed description and accompanying drawings, in which:

BRIEF DESCRIPTION OF THE DRAWINGS

The patent or application file contains a least one drawing executed in color. Copies of this patent or patent application publication with color drawings will be provided by the Office upon request and payment of the necessary fee.

DETAILED DESCRIPTION OF THE PREFERRED EMBODIMENT

Figure 1:
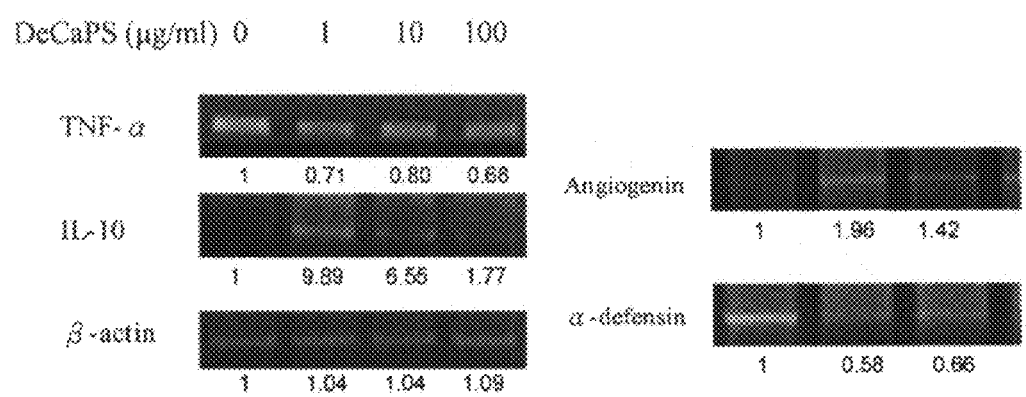
FIG. 1 is the PCR analysis showing the mRNA expression of cytokines and antimicrobial peptides in the intestinal epithelial cell-6 (IEC-6) cells treated with the DeCaPS (polysaccharide from *Dendrobii Herba*)

The invention is described more specifically with reference to the following embodiments. It is to be noted that the following descriptions of preferred embodiments of this invention are presented herein for the purpose of illustration and description only; it is not intended to be exhaustive or to be limited to the precise form disclosed.

The present invention provides a method for preparing a polysaccharide from a plant, including the steps of a) extracting the plant with a first alcohol to obtain a first extract, b) extracting the remaining material after step a) with a solvent to obtain a second extract, and c) precipitating the second extract with a second alcohol to obtain the polysaccharide.

EXAMPLE I

Preparation of Polysaccharides from *Dendrobium*

10 kg of fresh *Dendrobii Herba* was dried to obtain 2.92 kg of the dry material, and then the dry material was immersed and extracted with 73.3 L of methanol to form 136.79 gram of crude extract. The crude extract was treated with a de-methanol process, and then immersed in water overnight. The reaction solution was extracted with warm water at the temperature ranged from 55° C. to 60° C. for 30 minutes, and then centrifuged by centrifuge (ER-RC13 C124, HITACH) at 5,000 rpm and 10° C. After centrifugation, the supernatant was filtered through 6 μm of filter paper. The filtrate was precipitated with ethanol, and 20.684 g of polysaccharides (hereafter named as DeCaPS) were obtained.

EXAMPLE II

Immune Responses of IEC-6 Cells Treated by the DeCaPS a. Culture of IEC-6 Cells

IEC cells, which originated from the small intestine of the normal rats were cultured in Dulbecco's Modified Eagle Medium (DMEM) containing 5% fetal bovine serum, 4.5 g/L glucose, 5 μg/ml bovine insulin and 2 mM L-glutamine in an incubator with 5% $CO_2$ at 37° C.

b. The IEC-6 Cells were Treated with the DeCaPS

When the IEC-6 cells were confluent in the 6-well plate, the IEC cells were treated with DeCaPS at the concentrations of 1 μg/ml, 10 μg/ml and 100 μg/ml, respectively, for 6 hours.

c. The Isolation of Total RNA from the IEC Cells Treated with the DeCaPS

After the treatment with the DeCaPS, the IEC cells were harvested and suspended in 1 ml of Ultraspec™ RNA isolation Kit (a brand name, Biotex laboratories Inc. (USA)), and the total RNA was obtained by following the standard protocol of the kit. The total amount of obtained RNA was quantitatively determined.

d. Reverse-transcription and PCR Analysis of Cytokines and Toll-like Receptors

The reaction had the reaction volume of 26.5 μl and included 0.1 μg of oligo dT, 5 μg of the obtained total RNA and diethyl pyrocarbonate (DEPC)-treated sterilized water. The reaction was performed at 70° C. for 10 minutes. Then, 4 μl of 10 mM dNTP, 0.5 μl of rinsing, 1 μl of AMV (Avian Myeloblastosis virus) reverse transcriptase (10 unit) and 8 μl of 5× reverse transcriptase (RT) buffer was added so as to have the total volume of 40 μl. The mixture was incubated at 42° C. for 60 minutes, then at 90° C. for 5 minutes, and thereby the cDNA products were obtained. Subsequently, 0.5 μl of 10 mM deoxynucleotide triphosphate (dNTP), 0.5 μl of Prozyme DNA polymerase (2 unit), 2.5 μl of 10× Prozyme buffer, the primers (0.8 μl of 5 μM sense DNA and 0.8 μl of 5 μM antisense DNA) and sterilized water were added into 2.5 μl of the cDNA products to form a total volume of 25 μl of the mixture, and the mixture was incubated in a DNA thermal cycler (Perkin-Elmer-Cetus), and thereby the PCR was performed for 35 cycles. Sense and antisense primers, including sense and antisense sequences [SEQ ID NOS: 1-32] for the target genes and the corresponding annealing temperature are listed in the following table I.

TABLE I

| SEQ ID NO. | Target gene (PCR product size) | Annealing temperature (° C.) |
|---|---|---|
| 1, 2 | β-actin (510 bps) | 57 |
| 3, 4 | IL-1β (563 bps) | 61 |
| 5, 6 | IL-2 (502 bps) | 61 |
| 7, 8 | IL-4 (399 bps) | 61 |
| 9, 10 | Il-6 (638 bps) | 61 |
| 11, 12 | IL-10 (455 bps) | 61 |
| 13, 14 | TNF-α (308 bps) | 57 |
| 15, 16 | IFN-γ (460 bps) | 61 |

TABLE I-continued

| SEQ ID NO. | Target gene (PCR product size) | Annealing temperature (° C.) |
|---|---|---|
| 17, 18 | TGF-β (525 bps) | 61 |
| 19, 20 | Rat α-defensin (900 bps) | 59 |
| 21, 22 | Rat angiogenin (900 bps) | 59 (hot start) |
| 23, 24 | TLR2 (495 bps) | 55 |
| 25, 26 | TLR4 (508 bps) | 57 |
| 27, 28 | TLR5 (737 bps) | 59 |
| 29, 30 | TLR7 (729 bps) | 59 |
| 31, 32 | TLR9 (725 bps) | 60 |

FIG. 1 shows the mRNA expression of cytokines and antimicrobial peptides in the IEC-6 cells treated with the DeCaPS. After being treated with 1 μg/ml, 10 μg/ml and 100 μg/ml of the DeCaPS for 6 hours, the mRNA expression of Tumor Necrosis Factor-alpha (TNF-α) [SEQ ID NO: 33] in the IEC-6 cells was suppressed by about 29%, 20% and 30%; however, the mRNA expression of IL-10 [SEQ ID NO: 34] in the IEC-cells was enhanced up to 9.89-fold, 6.55-fold, and 1.77-fold, respectively. It is shown that the intestinal epithelial cells can be induced by the DeCaPS to provide tolerance signals to other cells in the immune system, so as to trigger the T helper 2/3 (TH2/3) pathways. In addition, after being treated with 1 μg/ml, 10 μg/ml and 100 μg/ml of DeCaPS for 6 hours, the mRNA expression of α-defensin [SEQ ID NO: 35] was suppressed by about 42%, 33% and 51%; however, the mRNA expression of angiogenin [SEQ ID NO: 36] was enhanced up to 1.96-fold, 1.42-fold, and 1.70-fold, respectively.

Figure 2:
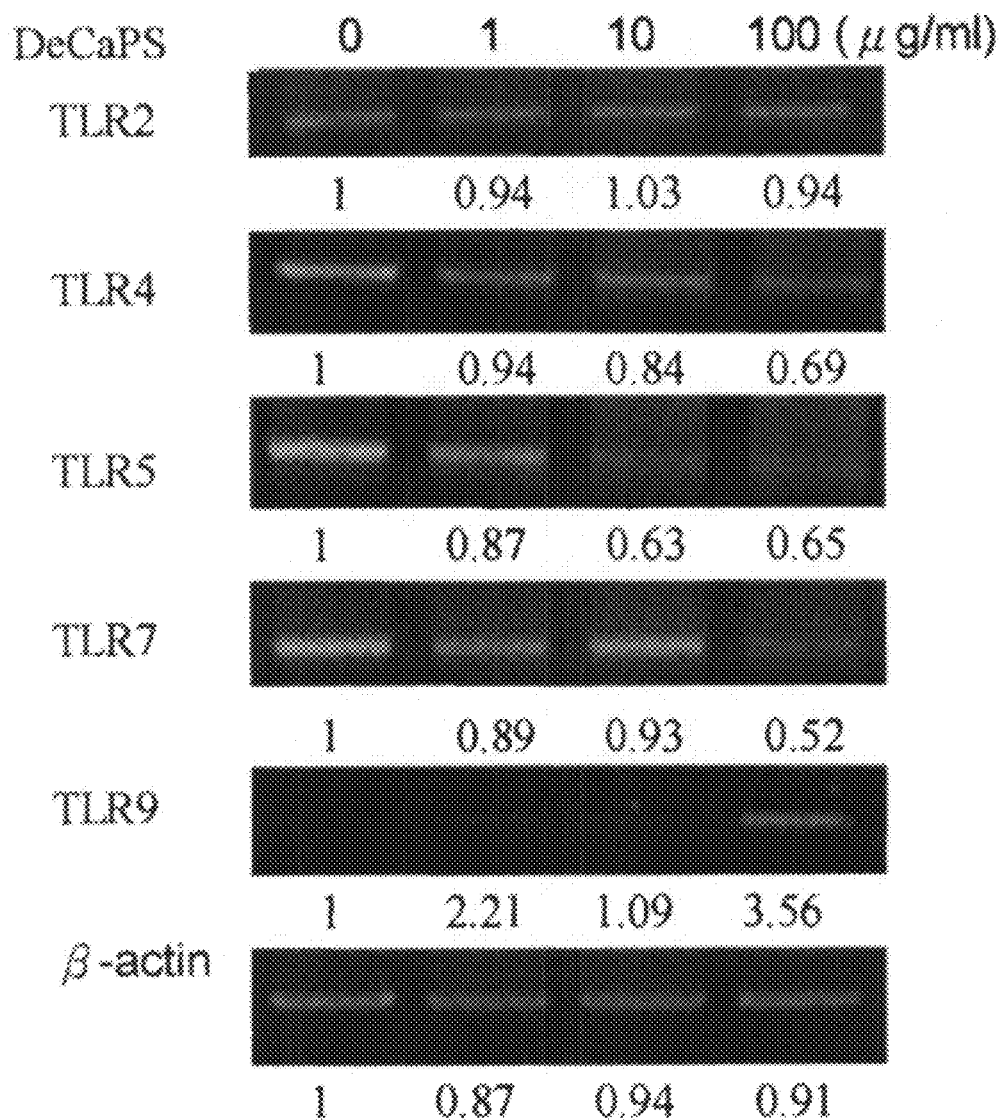
FIG. 2 is the PCR analysis showing the mRNA expressions of toll-like receptors in the IEC-6 cells treated with the DeCaPS.

As shown in FIG. 2, IEC-6 cell Toll like receptor 2 (TLR2) [SEQ ID NO: 37], Toll like receptor 4 (TNR4) [SEQ ID NO: 38], Toll like receptor 7 (TLR7) [SEQ ID NO: 39] and Toll like receptor 9 (TLR9) [SEQ ID NO: 40] were expressed without the DeCaPS treatment. After being treated with 1 μg/ml, 10 μg/ml and 100 μg/ml of the DeCaPS for 6 hours, the mRNA expression of TLR4 [SEQ ID NO: 38] in the IEC-6 cells was suppressed by about 6%, 16% and 13%, the mRNA expression of TLR5 [SEQ ID NO: 41] in the IEC-6 cells was suppressed by about 13%, 37% and 35%, and the mRNA expression of TLR7 [SEQ ID NO: 39] in the IEC-6 cells was suppressed by about 11%, 7% and 48%, respectively; however, the mRNA expression of TLR9 [SEQ ID NO: 40] was enhanced up to 2.21 fold, 1.09-fold and 3.56-fold, respectively. It is shown that the polysaccharides derived from *Dendrobium* not only suppress the expression of TNF-α [SEQ ID NO: 33], but also suppress the expression of TLR4 [SEQ ID NO: 38], TLR5 [SEQ ID NO: 41], and TLR7 [SEQ ID NO: 39].

EXAMPLE III

Effects on the Immune System by Oral Administration of DeCaPS in the Animal Model The C3H mice (13 weeks old) were fed with the DeCaPS, prepared from the Example I, via the drinking water at the dosages of 10 mg/kg/day, 50 mg/kg/day and 250 mg/kg/day for 5 days, and then were sacrificed to obtain the spleens and the bone marrows thereof.

a. Methy Thiazolyl Tetrazolium (MTT) Assays for Concanavalin A-stimulated Splenocytes from the C3H Mice The splenocytes ($4 \times 10^5$ cells/well) obtained from the C3H mice (a strain name) treated with the DeCaPS were cultured in Roswell Park Memorial Institute-1640 (RPMI-1640) medium containing 10% fetal bovine serum and 1 and 5 μg/ml concanavalin A (ConA) for 72 hours, and then treated with 1 mg/ml MTT for 3 hours. Then, lysis buffer containing 50% DMF and 20% sodium dodecyl sulphatehh (SDS) was added to the cell cultures, and the reactions were performed for 16 hours. The absorption of light at 570 nm for the reactions was analyzed to denote the growth index, as shown in FIG. 3.

Figure 3:
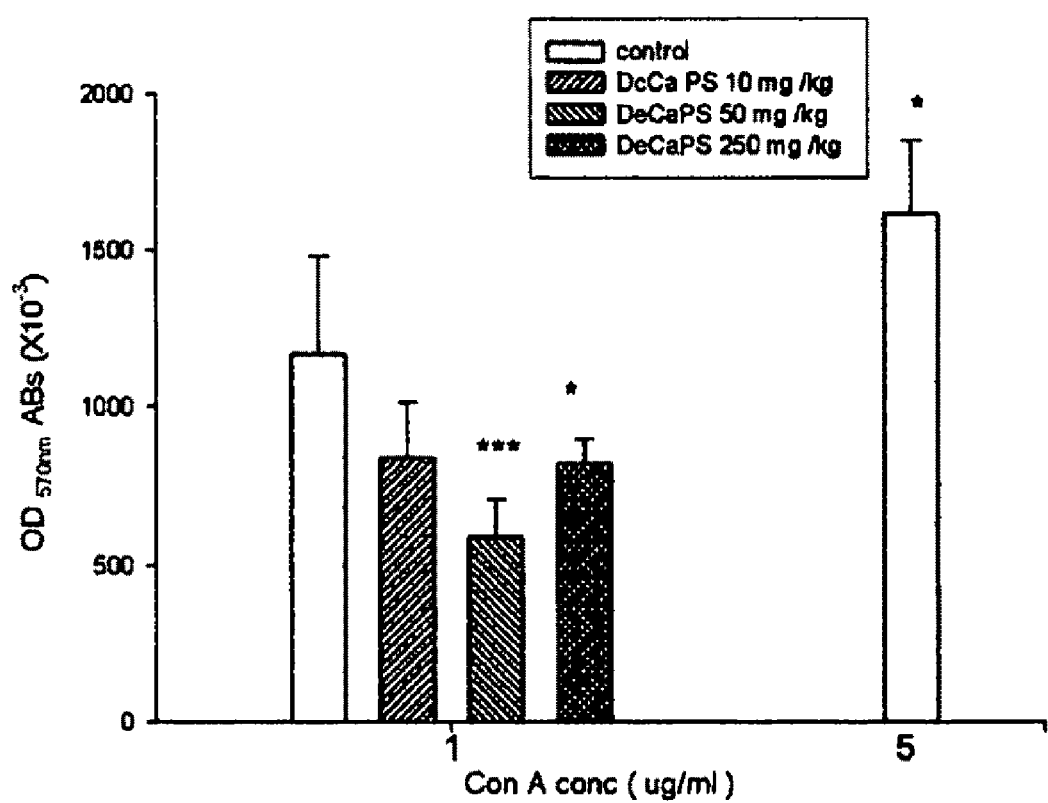
FIG. 3 is a chart showing the effects on the mitogenic responses of ConA-stimulated splenocytes from the C3H mice orally treated with the DeCaPS.

As shown in FIG. 3, after the C3H mice were orally treated with DeCaPS at dosages of 10 mg/kg/day, 50 mg/kg/day and 250 mg/kg/day for 5 days, the response to the 1 µg/ml ConA stimulation of the splenocytes were suppressed by about 28%, 49% and 30%.

b. MTT Assays for Granulocyte-macrophage Colony Stimulating Factor (GM-CSF)-stimulated Bone Marrow Cells Obtained from the C3H Mice Bone marrow cells were obtained from the legs of the C3H mice treated with DeCaPS. The bone marrow cells were cultured in Alpha Modification of Eagle's Medium ($\alpha$-MEM) containing 2% FCS and 4 ng/ml of GM-CSF for 72 hours, and the positive control group of bone marrow cells was cultured in $\alpha$-MEM containing 2% FCS and 20 ng/ml of GM-CSF for 72 hours. Then, the medium was replaced by RPMI-1640 containing 1 mg/ml MTT and 2% FCS for 3 hours and the cells were further treated with MTT lysis buffer (20% SDS and 50% DMF at pH4.5) overnight. The absorption of light at 570 nm for the reactions was analyzed to denote the growth index, as shown in FIG. 4.

Figure 4:
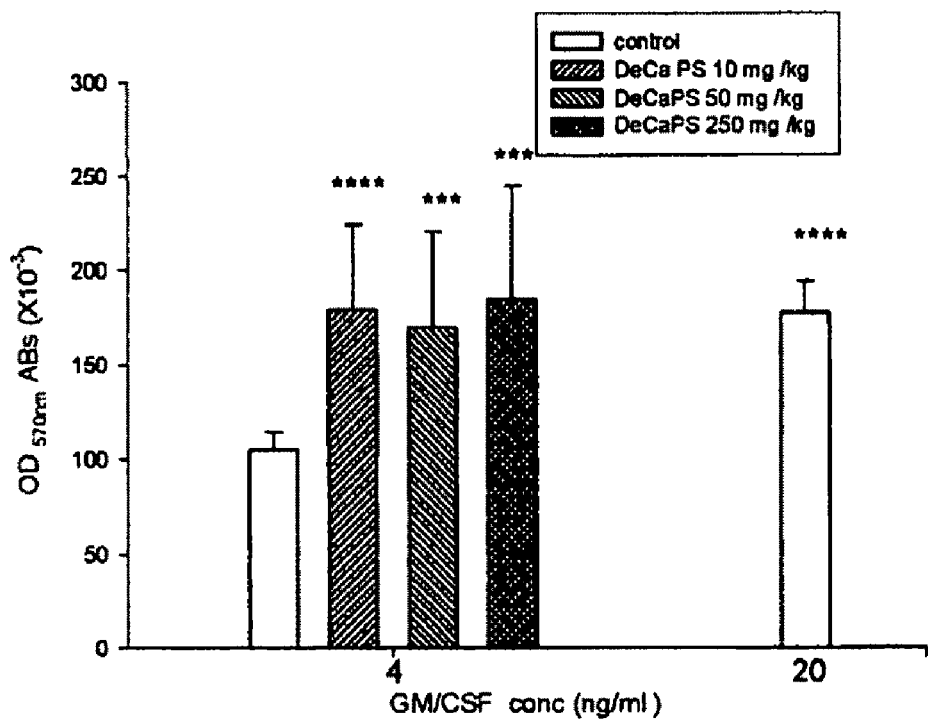
FIG. 4 is a chart showing the effects on the mitogenic responses of GM-CSF stimulated bone marrow cells from the C3H mice orally treated with the DeCaPS.

Please refer to FIG. 4, which shows the effects on the mitogenic responses of GM-CSF-stimulated bone marrow cells obtained from the C3H mice orally treated with the DeCaPS. As shown in FIG. 4, after the C3H mice were respectively and orally treated with DeCaPS at the dosages of 10 mg/kg/day, 50 mg/kg/day and 250 mg/kg/day for 5 days, the mitogenic response of the GM-CSF-stimulated bone marrow cells was enhanced up to 1.71-fold, 1.62-fold, and 1.76-fold.

c. mRNA Expression of Cytokines in Peyer's Patch and Splenocytes Obtained from the C3H Mice The Peyer's patch and splenocytes were obtained from the C3H mice treated with the DeCaPS. PCR analysis of the mRNA expression of the specific cytokines in Peyer's patch and the splenocytes was performed by the method described in Example II, and the PCR results were shown in FIG. 5, wherein the lanes 1-4 denote the C3H mice orally treated with the DeCaPS at the dosages of 0 mg/kg/day, 10 mg/kg/day, 50 mg/kg/day and 250 mg/kg/day, respectively.

Figure 5:
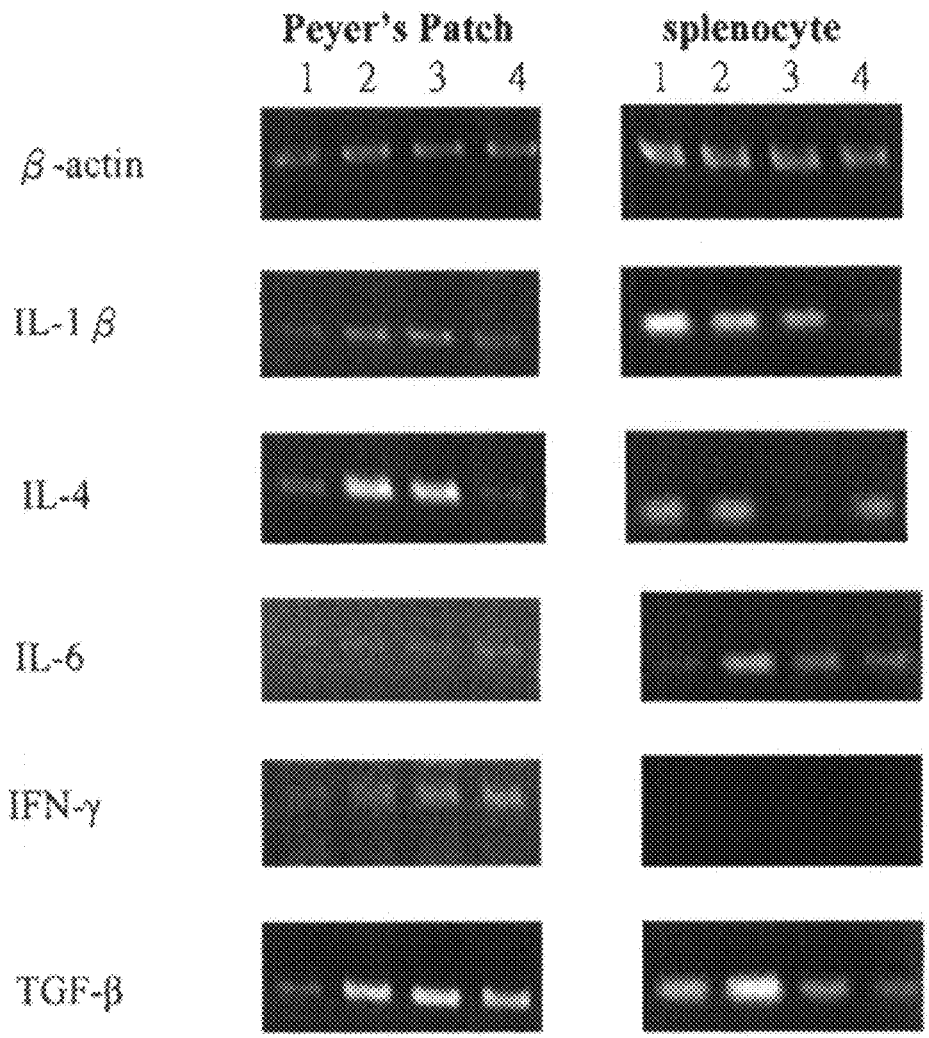
FIG. 5 is the PCR analysis showing cytokine-specific mRNA expression_in Peyer's patch and splenocytes obtained from the C3H mice orally treated with the DeCaPS.

As shown in FIG. 5, after the C3H mice were orally treated with the DeCaPS for 5 days, the mRNA expression of IL-4 [SEQ ID NO: 42], IL-6 [SEQ ID NO: 43], IL-1$\beta$ [SEQ ID NO: 44], IFN-$\gamma$ [SEQ ID NO: 45] and TGF-$\beta$ [SEQ ID NO: 46] in Peyer's patch was increased. After the C3H mice were orally treated with the DeCaPS at the dosages of 10 mg/kg/day and 50 mg/kg/day for 5 days, the mRNA expression of IL-4 [SEQ ID NO: 42] was enhanced up to 2.64-fold and 2.46-fold, respectively. After the C3H mice were orally treated with DeCaPS at the dosages of 10 mg/kg/day, 50 mg/kg/day and 250 mg/kg/day for 5 days, the mRNA expression of IL-6 [SEQ ID NO: 43] was respectively enhanced up to 2.61-fold, 3.99-fold, and 5.35-fold, the mRNA expression of IL-1 $\beta$[SEQ ID NO: 44] was respectively enhanced up to 1.83 fold, 2.00-fold, and 1.11-fold, the mRNA expression of IFN-$\gamma$ [SEQ ID NO: 45] was respectively enhanced up to 3.47-fold, 5.47-fold and 5.57-fold, and the mRNA expression of TGF-$\beta$ [SEQ ID NO: 46] was respectively enhanced up to 2.38-fold, 2.54-fold, and 1.89-fold. The increments of IL-4 [SEQ ID NO: 42] and IL-6 [SEQ ID NO: 43] suggests that Th2 pathway is triggered, and T helper cells are activated by the increments of IL-1$\beta$ [SEQ ID NO: 44] to secrete cytokines, such as TGF-$\beta$ [SEQ ID NO: 46]. This may trigger the IgA class switched B cells, which are induced by TGF-$\beta$ [SEQ ID NO: 46] to secrete IgA so as to suppress certain immune responses.

As also shown in FIG. 5, after the C3H mice were orally treated with the DeCaPS for 5 days, the mRNA expression of IL-1 $\beta$ [SEQ ID NO: 44], IL-4 [SEQ ID NO: 42] and TGF-$\beta$ [SEQ ID NO: 46] in the splenocytes was suppressed. After the C3H mice were orally treated with DeCaPS at the dosages of 10 mg/kg/day, 50 mg/kg/day and 250 mg/kg/day for 5 days, the mRNA expression of IL-1 $\beta$ [SEQ ID NO: 44] was suppressed by about 32%, 43% and 79%, and the mRNA expression of IL-4 [SEQ ID NO: 42] was suppressed by about-7%, 67% and 14%. After the C3H mice were orally treated with DeCaPS at the dosages of 50 mg/kg/day and 250 mg/kg/day for 5 days, the mRNA expression of TGF-$\beta$ [SEQ ID NO: 46] was suppressed by about 27% and 44%, and the mRNA expression of IFN-$\gamma$ [SEQ ID NO: 45] was suppressed by about 33% and 97%, respectively. However, after the C3H mice were orally treated with the DeCaPS at the dosages of 10 mg/kg/day, 50 mg/kg/day and 250 mg/kg/day for 5 days, the mRNA expression of IL-6 [SEQ ID NO: 43] was enhanced up to 1.84-fold, 1.4-fold and 1.23-fold. It is to be noted that there are not significant cellular responses to DeCaPS treatment, and this phenomenon is consistent with the responses to the ConA stimulations.

EXAMPLE IV

Enhancement of Oral Tolerance in an Animal Model by DeCaPS

Since it is well-known that animals can be immunized by ovalbumin (OVA) to establish the animal model for the autoimmune disease (*The Journal of Pharmacology and Experimental Therapeutics* 288:849-857, 1999), the present invention establishes an animal model which includes mice with OVA-induced autoimmune disease, and the mice are treated with DeCaPS to enhance oral tolerance. C57/BL6j mice (65 weeks old) were orally treated with 0.5 mg/ml ovalbumin (OVA) in drinking water at day 4 and day 5, and DeCaPS was administrated to the C57/BL6j mice as an adjuvant at dosages of 10 mg/kg/day, 40 mg/kg/day and 160 mg/kg/day at days 3-7. 50 µg of OVA with Complete Freund's Adjuvant (CFA) was administrated to the mice as an antigen via i.p. injection at day 8 and with OVA on day 24. OVA-specific IgG and IgM in the blood was collected at day 22 and day 30. The mice were sacrificed at day 32 to collect an intestinal lavage solution of the intestinal mucosa and the lung mucosa to detect IgA in response to OVA. The detailed experimental procedures are illustrated in the following table II.

TABLE II

Oral administration of OVA with/without DeCaPS in animal model

| Group | Amount of mice | Blood collection | Oral OVA | Oral DeCaPS | OVA + CFA Injection | OVA injection |
|---|---|---|---|---|---|---|
| Normal | 5 | Days 0, 22, 30 | — | — | Day 8 | Day 24 |
| Control | 6 | Days 0, 22, 30 | Days 4-5 | — | Day 8 | Day 24 |
| Positive Control | 6 | Days 0, 22, 30 | Days 1-5 | — | Day 8 | Day 24 |
| DC-1 (10 mg/kg/day) | 5 | Days 0, 22, 30 | Days 4-5 | Days 3-7 | Day 8 | Day 24 |
| DC-2 (40 mg/kg/day) | 5 | Days 0, 22, 30 | Days 4-5 | Days 3-7 | Day 8 | Day 24 |
| DC-3 (160 mg/kg/day) | 5 | Days 0, 22, 30 | Days 4-5 | Days 3-7 | Day 8 | Day 24 |

Figure 6:
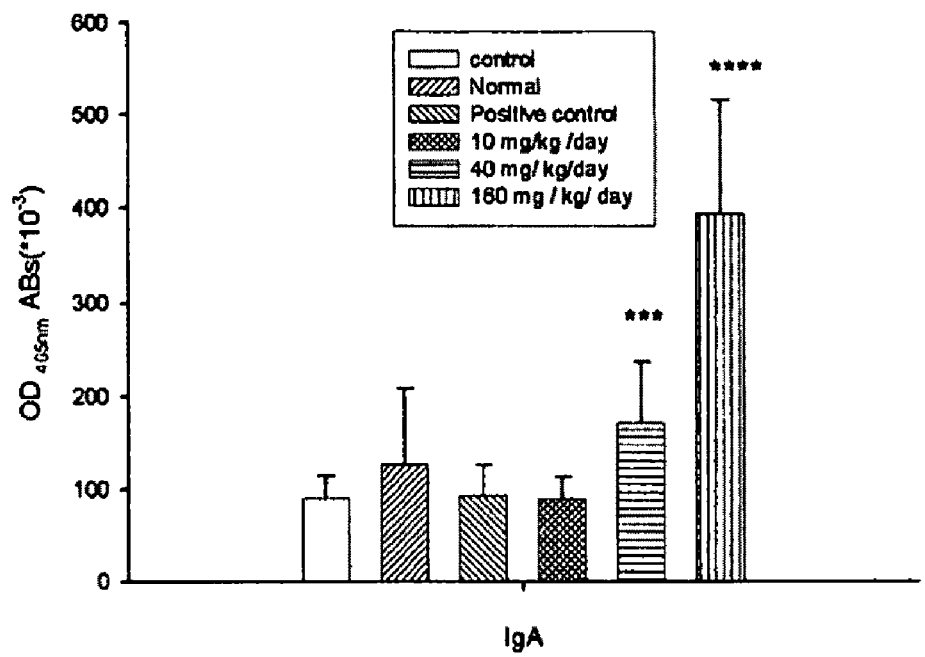
FIG. 6 is a chart showing the titers of the ovalbumin specific IgA in the intestinal lavage solution from the C57BL/6j mice (a strain name) orally immunized by the ovalbumin with or without administration of DeCaPS.

The intestinal lavage solution of the intestinal mucosa was obtained from the mice at the day 32, and the titer of the ovalbumin-specific IgA in the intestinal lavage solution was determined as shown in FIG. 6. Referring to FIG. 6, IgA secreted from the intestinal mucosa was enhanced up to 1.9-fold ($p<0.01$) in the C57BL6j mice treated by the OVA with DeCaPS at the dose of 40 mg/kg/day, and the IgA secreted from the intestinal mucosa was enhanced up to 4.35-fold ($p<0.001$) in the C57/BL6j mice treated by the OVA with DeCaPS at the dose of 160 mg/kg/day.

Figure 7:
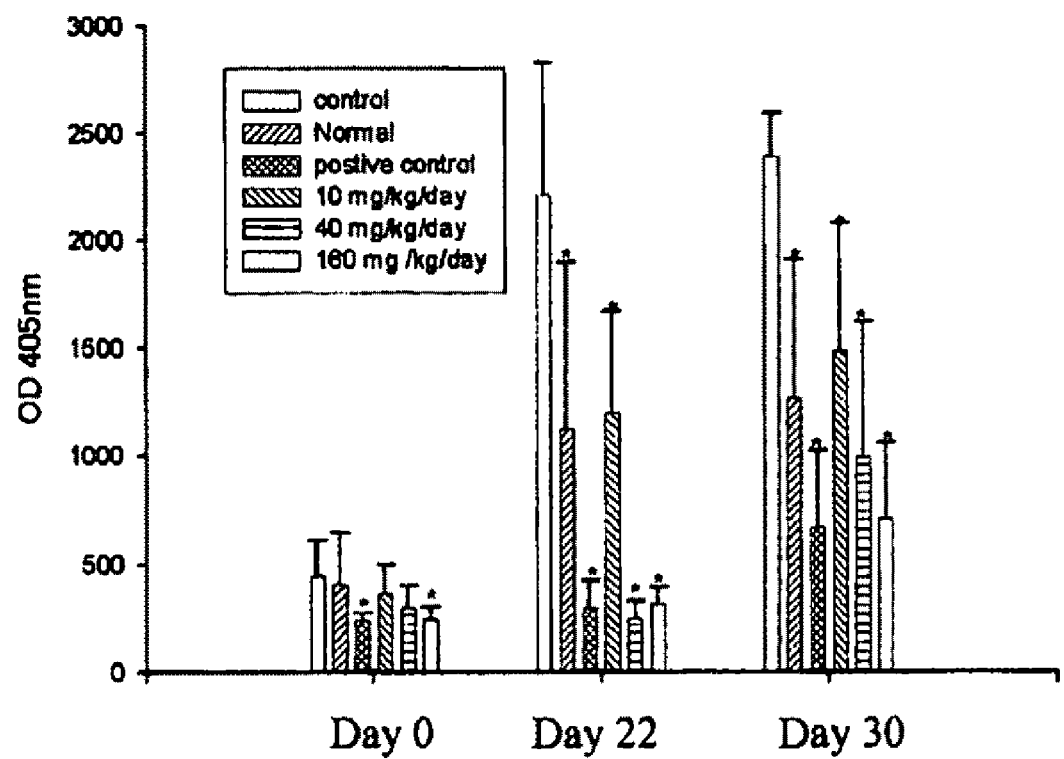
FIG. 7 is a chart showing the titers of the ovalbumin specific immunoglobulin M (IgM) in serum from the C57BL/6j mice orally immunized by the ovalbumin with or without administration of DeCaPS.

The titer of IgM antibodies in the blood at the day 22 and day 30 were determined, as shown in FIG. 7. With comparison to the IgM antibody level expressed in the control group at day 22, the IgM antibody level expressed in the normal group was decreased by about 49% ($p<0.05$), the IgM antibody level-expressed in the positive control group was suppressed by about 87% ($p<0.05$), the IgM antibody level-expressed in the DC-1 group was suppressed by about 46% ($p<0.02$), the IgM antibody level-expressed in the DC-2 group was suppressed by about 88% ($p<0.001$), and the IgM antibody level in the DC-3 group was suppressed by about 86% ($p<0.001$). Furthermore, with comparison to the IgM antibody level-expressed in the control group at day 30, the IgM antibody level-expressed in the normal group was decreased by about 47% ($p<0.01$), the IgM antibody level-expressed in the positive control group was suppressed by about 72% ($p<0.001$), the IgM antibody level expressed in the DC-1 group was suppressed by about 38% ($p<0.01$), the IgM antibody level expressed in the DC-2 group was suppressed by about 58% ($p<0.01$), and the IgM antibody level expressed in the DC-3 group was suppressed by about 71% ($p<0.001$).

Figure 8:
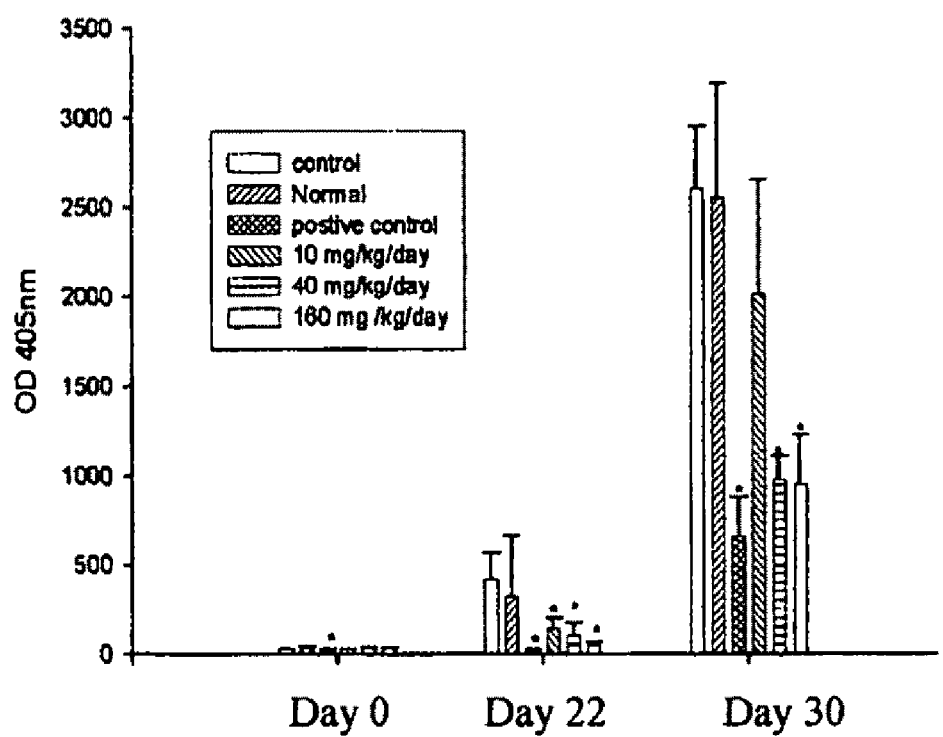
FIG. 8 is a chart showing the titers of the ovalbumin specific immunoglobulin G (IgG) in serum from the C57BL/6j mice orally immunized by the ovalbumin with or without administration of DeCaPS.

The titer of IgG antibodies in the blood at day 22 and day 30 were determined, as shown in FIG. 8. With comparison to the IgG antibody level expressed in the control group at the day 22, the IgG antibody level-expressed in the positive control group was suppressed by about 94% ($p<0.01$), the IgG antibody level expressed in the DC-1 group was suppressed by about 67% ($p<0.01$), the IgG antibody level expressed in the DC-2 group was suppressed by about 76% ($p<0.01$), and the IgG antibody level expressed in the DC-3 group was suppressed by about 88% ($p<0.001$). Furthermore, with comparison to the IgG-antibody level expressed in the control group at day 30, the IgG antibody level expressed in the positive control group was suppressed by about 75% ($p<0.001$), the IgG antibody level-expressed in the DC-2 group was suppressed by about 62% ($p<0.001$), and the IgG antibody level expressed in the DC-3 group was suppressed by about 63% ($p<0.001$).

Figure 9:
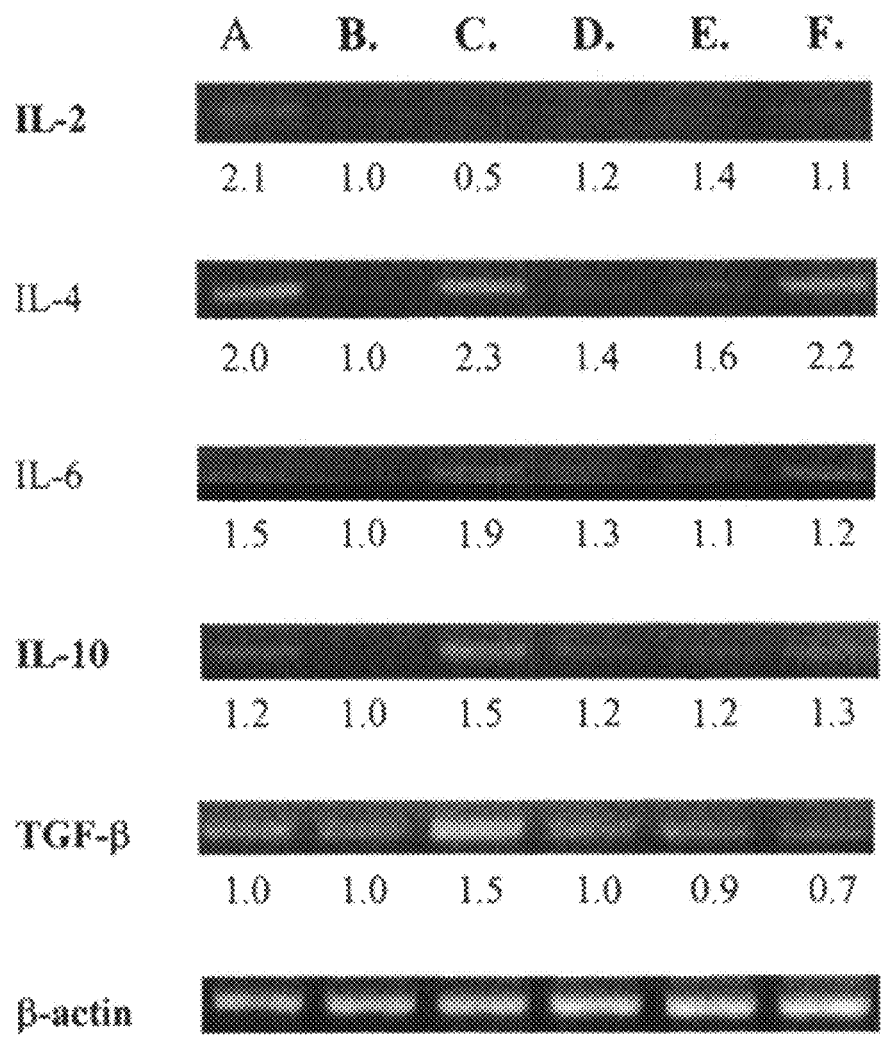
FIG. 9 is the PCR analysis showing the cytokine expressions of lymphocytes in Peyer's patch from the C57BL/6j mice.

In addition, Peyer's patch was obtained from the mice at day 32 and the mRNA of the cytokines expressed by the lymphocytes in Peyer's patch was extracted and analyzed. The results are shown in FIG. 9, wherein lane A denotes the normal group, lane B denotes the control group, lane C denotes the positive control group, lane D denotes the DC-1 group, lane E denotes the DC-2 group, and lane F denotes the DC-3 group. PCR amplification was programmed to denature at 94° C. for 45 seconds, anneal at 61° C. for 45 seconds and extension for 72° C. for 1 minute. There were 37 cycles in the PCR program. The PCR products were separated by electrophoresis in a 2% agarose gel and the gel was stained with ethidium bromide and visualized under UV light.

With comparison to the control group, the TGF-β [SEQ ID NO: 46] level expressed in the DC-3 group was suppressed about 30%, the IL-4 [SEQ ID NO: 42] level expressed in the DC-3 group was enhanced up to 2.2-fold, and the IL-10 [SEQ ID NO: 34] level expressed in the DC-3 group was enhanced up to 1.3-fold. With comparison to the control group, the IL-2 [SEQ ID NO: 47] level expressed in the DC-2 group was enhanced up to 1.4-fold, and the IL-4 [SEQ ID NO: 42] level expressed in the DC-2 group was enhanced up to 1.6-fold. Moreover, with comparison to the control group, the IL-4 [SEQ ID NO: 42] level expressed in the DC-1 group was enhanced up to 1.4-fold, and the IL-6 [SEQ ID NO: 43] level expressed in the DC-1 group was enhanced up to 1.3-fold.

The mRNA expression of IL-4 [SEQ ID NO: 42] and IL-6 [SEQ ID NO: 43] was enhanced in the lymphocytes in Peyer's patch. It is to be emphasized that since Payer's patch is the site for the determination of immune responses to antigens, when the antigen-primed T or B cells back to intestine through homing mechanism, the Th2 pathway is activated to produce antibodies in response to the increments of IL-4 [SEQ ID NO: 42] and IL-6 [SEQ ID NO: 43], the IgG and IgM expressions in the serum are suppressed so as to suppress the allergenic responses, and oral tolerance is achieved.

In view of aforesaid descriptions, the mitogenic response of T cells in the spleen is suppressed by polysaccharides of *Dendrobium*; however, granulocytes and macrophages in bone marrow are activated by polysaccharides of *Dendrobium*. In other words, T cells activated in autoimmune diseases can be suppressed by oral administration of polysaccharides of *Dendrobium*; however, the granulocyte lineage cells are activated by oral administration of polysaccharides of *Dendrobium* for preventing pathogen invasions by innate immunity promotion.

Regarding intestinal immunity, the mRNA expression of IL-4 [SEQ ID NO: 42], IL-6 [SEQ ID NO: 43], IL-1β[SEQ ID NO: 44], IFN-γ[SEQ ID NO: 45] and TGF-β [SEQ ID NO: 46] are enhanced to trigger the Th2/Th3 pathways in the intestine, so as to form oral tolerance. According to the expression of TNF-α [SEQ ID NO: 33], TLR2 [SEQ ID NO:

37], TLR4 [SEQ ID NO: 38], TLR5 [SEQ ID NO: 41] and TLR7 [SEQ ID NO: 39] in IEC-6 cells treated with the polysaccharides of *Dendrobium*, it is shown that the signals mediated by the toll-like receptors can be regulated to be immunosupressed or anti-inflammatory response by the polysaccharides of *Dendrobium*, so as to enhance the oral tolerance-associated signals, i.e. the Th2/3 pathways and maintain mucosal homeostasis during pathogenic status such as autoimmune disease and mucosal disorder. Interestingly, the expression of angiogenin, which has antimicrobial activities, can be induced by administration of the polysaccharides of *Dendrobium* as described in Example II. Accordingly, oral administration of polysaccharides of *Dendrobium* not only enhances oral tolerance, but also triggers innate immunity mechanisms for preventing pathogen invasions. According to these findings, polysaccharides of *Dendrobium* may have beneficial uses for treatment of autoimmune diseases and mucosal disorders such as inflammatory bowel disease (IBD) by releasing prolonged inflammation and further injury.

(PS3) using Fmoc Chemistry, purified by the Agilent HPLC and identified by the Brukeer esquire 2000 MS.

b. Administrations of IRBP and DeCaPS

Specific-pathogen-free (SPF) mice, C57BL/6j mice, were randomly grouped into a normal group, a control group, a DC-10 group, a DC-40 group and a DC-160 group, wherein there were 6 mice in each group. The human IRBP peptide [SEQ ID NO: 48] (150 µg/mouse) and CFA (1:1, vol/vol) in a 0.2 ml emulsion was administrated to each SPF mouse in the groups, except the normal group, via i.p. injection. The mice in the DC-10 group, DC-40 group, and the DC-160 group were fed with DeCaPS at a dosage of 10 mg/kg/day, 40 mg/kg/day and 160 mg/kg/day, resepectively, for 28 days. Retinal functions of the mice were determined by an electroretinogram (ERG) analysis, and the mice were sacrificed at day 28 to obtain the eyes thereof for the bioassays and histopathology. The experimental procedures are illustrated in the following table III.

TABLE III

Treatment of autoimmune disease with/without DeCaPS in animal model

| Group | Amount of mice | ERG determination | immunized with IRBP at day 1 | DeCaPS (days 1-28) mg/kg/day | DTK assay (days 21 and 23) | ERG & histopathology at day 28 |
|---|---|---|---|---|---|---|
| Normal | 6 | + | − | — | + | + |
| Control | 6 | + | + | — | + | + |
| DC-10 | 6 | + | + | 10 | + | + |
| DC-40 | 6 | + | + | 40 | + | + |
| DC-160 | 6 | + | + | 160 | + | + |

It has been disclosed that angiogenins have activities against not only enteric microbes such as *Enterococcus faecalis* but also microbes that cause systematic infections in humans such as *Candida albicans* and *Streptococcus pneumoniae*. (*Nat. Immunol.* 4:269-273, 2003) In clinical studies, leucorrhea in women is a polymicrobial, superficial vaginal infection. The infection is frequently caused by bacterias such as *G. vaginalis*, *Candida* spp, *C. albicans*, *T. vaginalis*, *Streptococcus* group D, *Streptococcus* b hemolytic, *E. coli*, and *Klebsiella* spp etc. (Salud publica Mex vol. 45 suppl. 5, pS694-S697, 2003). It is obvious that leucorrhea in women caused by microbes such as *Candida albicans* could be relieved by the activities of angiogenins, which are induced by the oral administration of polysaccharides of *Dendrobium*.

EXAMPLE V

Treatment of Autoimmune Disease by DeCaPS

Experimental autoimmune uveitis is a T-cell-mediated autoimmune disease that serves as a model for several ocular autoimmune diseases, which can induced by immunization with interphotoreceptor retinoid binding protein (IRBP), a 140-kD glycolipoprotein. Also, autoimmune uveitis can be induced by IRBP peptide 1-20 (SEQ ID NO. 48:GPTH-LFQPSLVLDMAKVLLD), the amino acids 1-20 of IRBP. In addition, the IRBP peptide 1-20 is conserved in mice and humans. (*Investigative Opthalmology & Visual Science* 41(1):127-131, 2000) Hence, the IRBP peptide was administrated to the C57BL/6j mice to establish the autoimmune disease model in the present invention.

a. Synthesis of IRBP Peptide

The IRBP peptide (SEQ ID NO. 48: GPTHLFQPSLVLD-MAKVLLD) was synthesized on the peptide synthesizer c. Delayed-type Hypersensitivity (DTH) Test On day 21 after immunization with the IRBP peptide, the mice were injected subcutaneously with 20 µg of the IRBP peptide emulsion in Incomplete Freund's Adjuvant, IFA, (20 µl) into the left footpad. The right footpad was injected with IFA only. After 48 hours, the thicknesses of the footpads were measured with a caliper.

Figure 10:
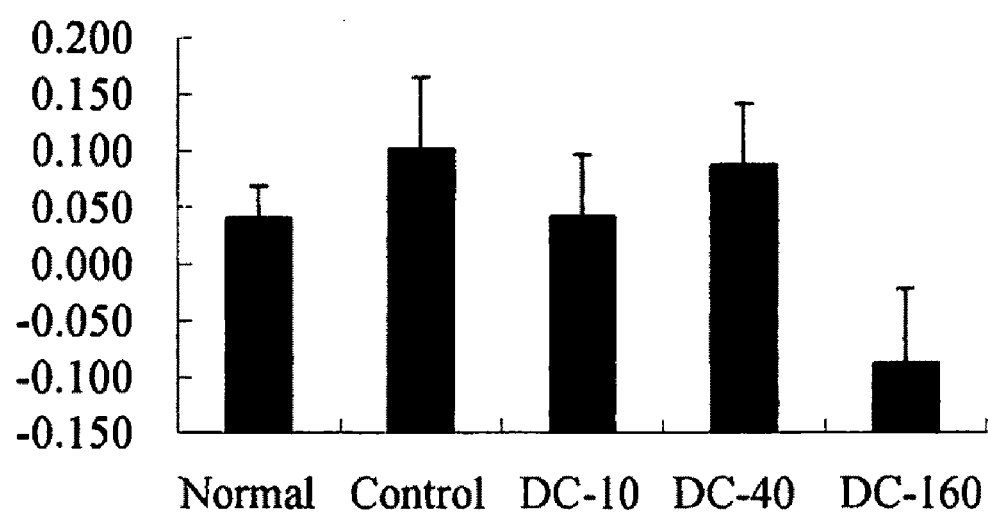
FIG. 10 is a chart showing the delayed-type hypersensitivity (DTH) responses of the C57BL/6j mice.

Please refer to FIG. 10, which shows the DTH responses of the mice. The DTH responses were shown by footpad increments in water volume relative to the footpad increment of the mice injected with the phosphate buffer saline (PBS). It is to be noted that the footpad increment of the mice co-treated with the DeCaPS at the dosage of 160 mg/kg/day is significantly decreased.

d. Electro-retinogram (ERG) Analysis

The mice were dark-adapted for 2 hours, and then anesthetized with sodium pentobarbital. Then, the corneas of the mice were anesthetized, and the pupils were dilated. The retinas were stimulated with a flash of light, and the responses of the retina to the flash of light were recorded as electroretinograms. The electroretinograms show the action of photoreceptors and functions of the proximal retina such as bioplar and Miller cells. The electroretinograms are used for reflecting the state of the entire retina. In electroretinograms, there is typically a negative-going a-wave, followed by a positive-going b-wave. The leading edge of the a-wave provides a direct measure of the activities of the cone and rod cells in the photoreceptor layer, while the b-wave provides a reflection of the action of bipolar cells in the inner nuclear layer.

Figure 11A:
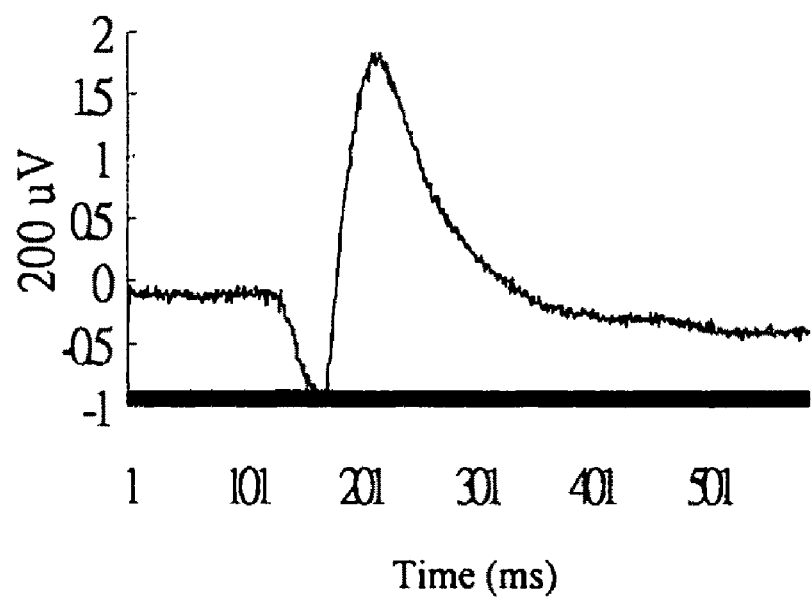
FIG. 11A is a chart showing the electro-retinograms to a range of flash intensities for the mice in the normal group.
Figure 11A:
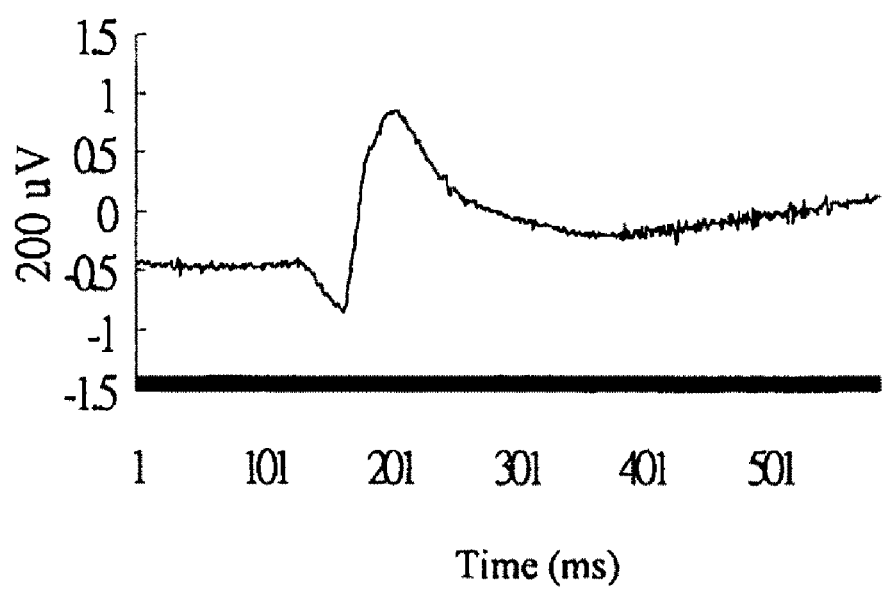

For the two mice randomly selected from the normal group at day 28, the results of the electroretinogram analysis are respectively shown in the upper part and the lower part of FIG. 11A, wherein the flash onset was at time 100 millisecond and the flash duration was approximately 600 milliseconds.

Figure 11B:
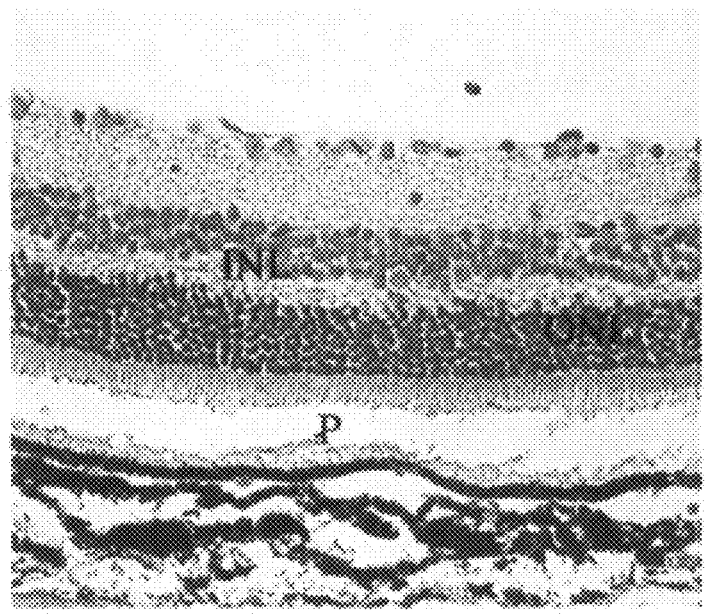
FIG. 11B is a diagram showing the histopathology of the eyes of the mice in the normal group.
Figure 11B:
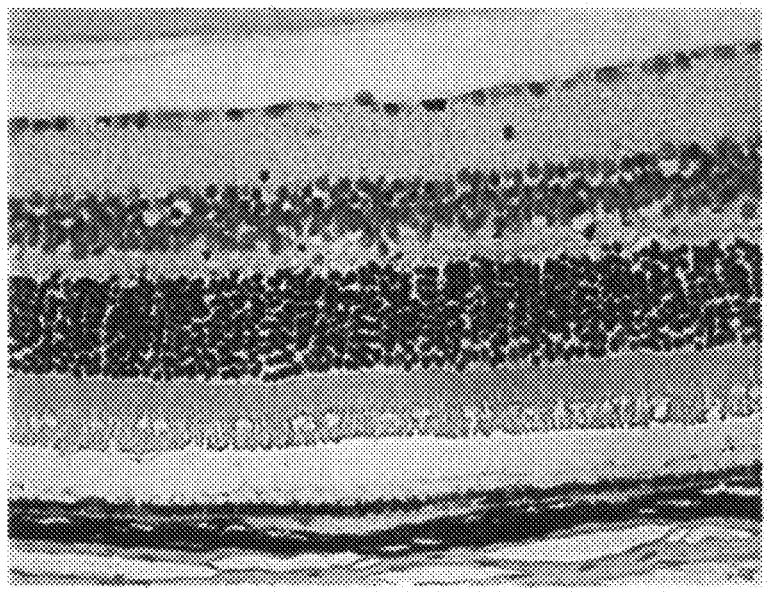

For the two mice randomly selected from the normal group at day 28, the histopathology of the eyes are respectively shown in the upper part and the lower part of FIG. 11B (400× magnification), wherein the photoreceptor layer is denoted as "P", the outer nuclear layer is denoted as "ONL", and the inner nuclear layer is denoted as "INL".

Figure 12A:
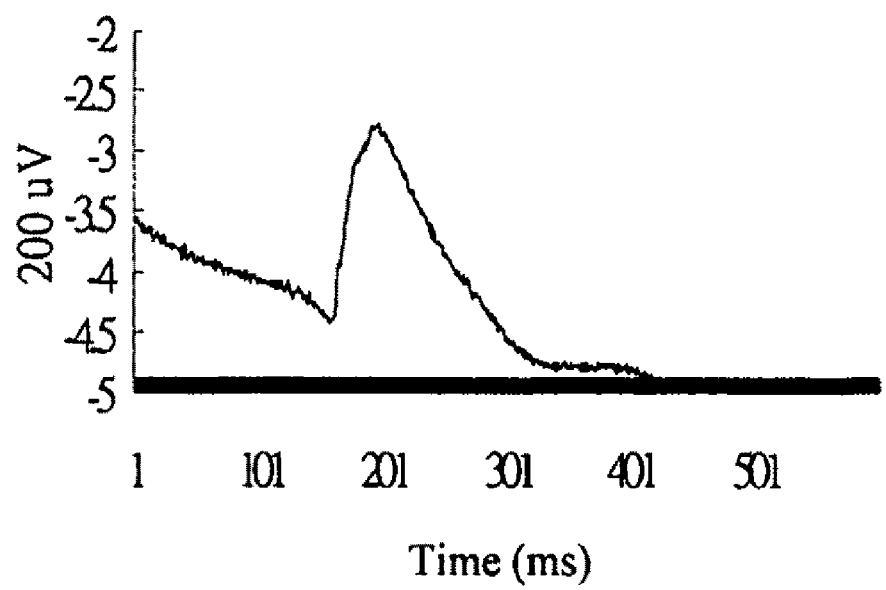
FIG. 12A is a chart showing the electro-retinograms for the mice in the control group.
Figure 12A:
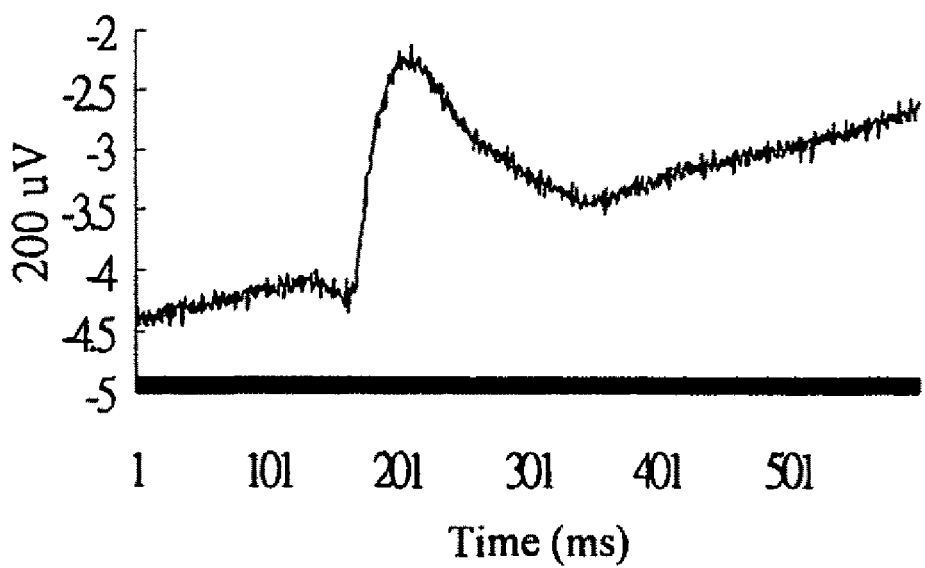
Figure 12B:
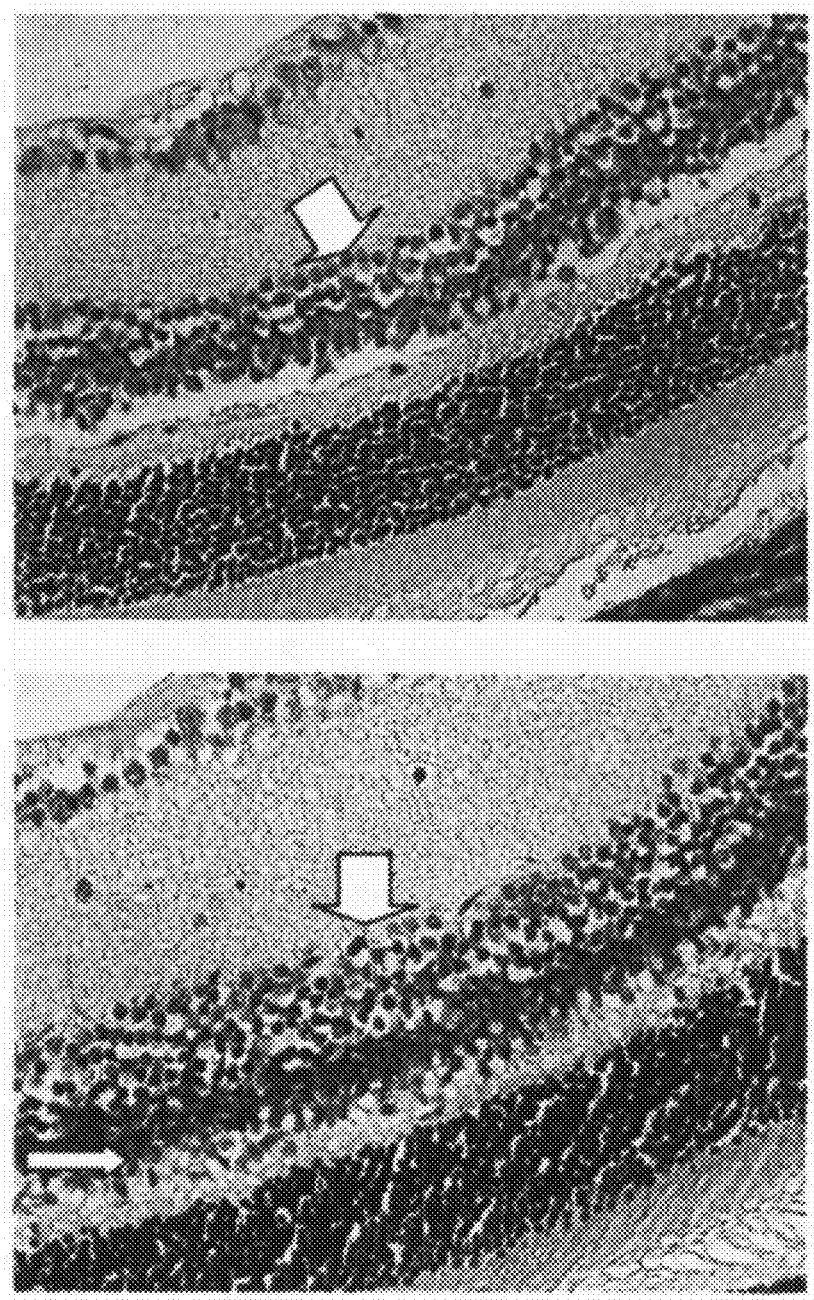
FIG. 12B is a diagram showing the histopathology of the eyes of the mice in the control group.

For two mice randomly selected from the control group at day 28 the results of the electroretinogram analysis are respectively shown in the upper part and the lower part of FIG. 12A, wherein the flash onset was at time 100 millisecond and the flash duration was approximately 600 milliseconds. For the two mice randomly selected from the control group at day 28, the histopathology of the eyes are respectively shown in the upper part and the lower part of FIG. 12B (400× magnification). It is shown that due to immunization with the IRBP peptide, the photoreceptor layer (P), the outer nuclear layer (ONL) and the inner nuclear layer (INL) of the mice in the control group are severely damaged.

Figure 13A:
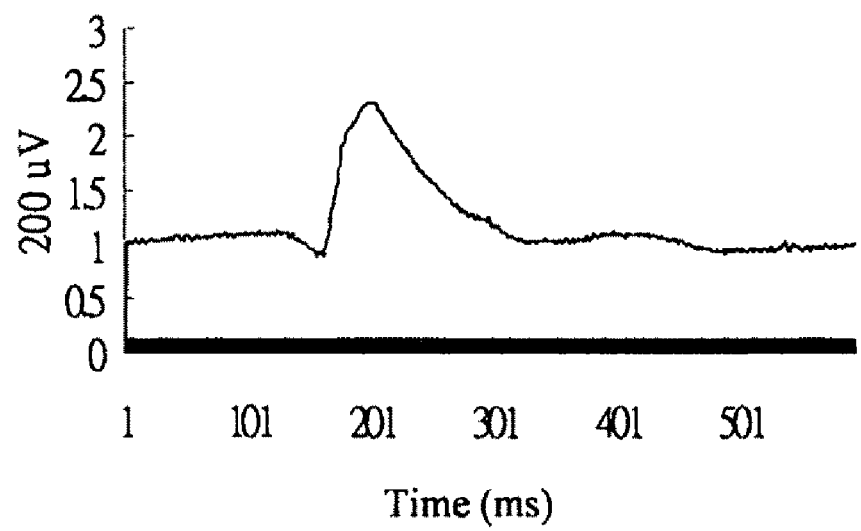
FIG. 13A is a chart showing the electro-retinograms or the mice in the DC-10 group.
Figure 13A:
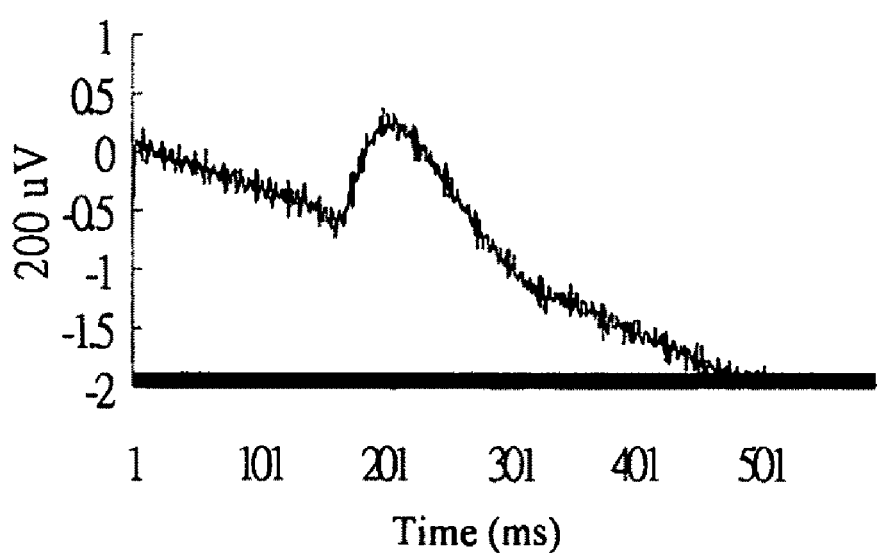
Figure 13B:
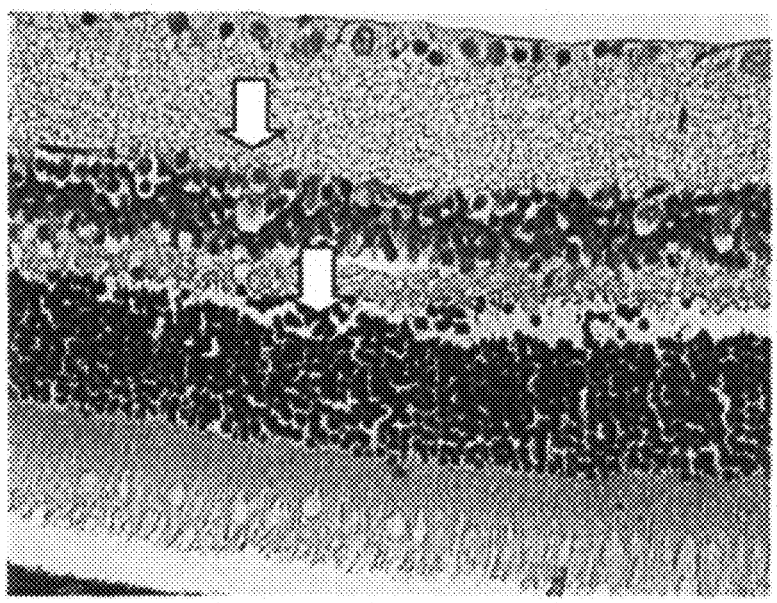
FIG. 13B is a diagram showing the histopathology of the eyes of the mice in the DC-10 group.
Figure 13B:
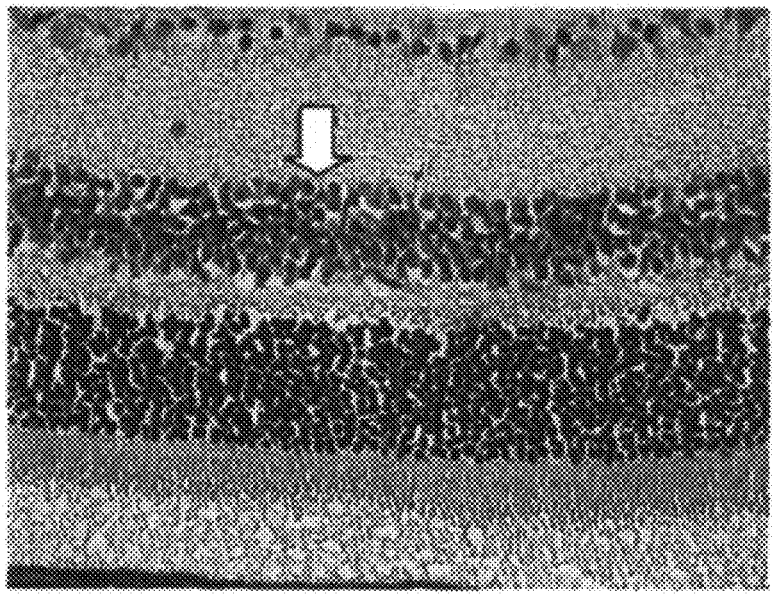

For the two mice randomly selected from the DC-10 group at the day 28, the results of the electroretinogram analysis are respectively shown in the upper part and the lower part of FIG. 13A, wherein the flash onset was at time 100 millisecond and the flash duration was approximately 600 milliseconds. For the two mice randomly selected from the DC-10 group at day 28, the histopathology of the eyes were are respectively shown in the upper part and the lower part of FIG. 13B (400× magnification). It is shown that after immunization with the IRBP peptide and oral administration of the DeCaPS (10 mg/kg/day) for 28 days, the photoreceptor layer (P), the outer nuclear layer (ONL) and the inner nuclear layer (INL) of the mice in the DC-10 group are severely damaged.

Figure 14A:
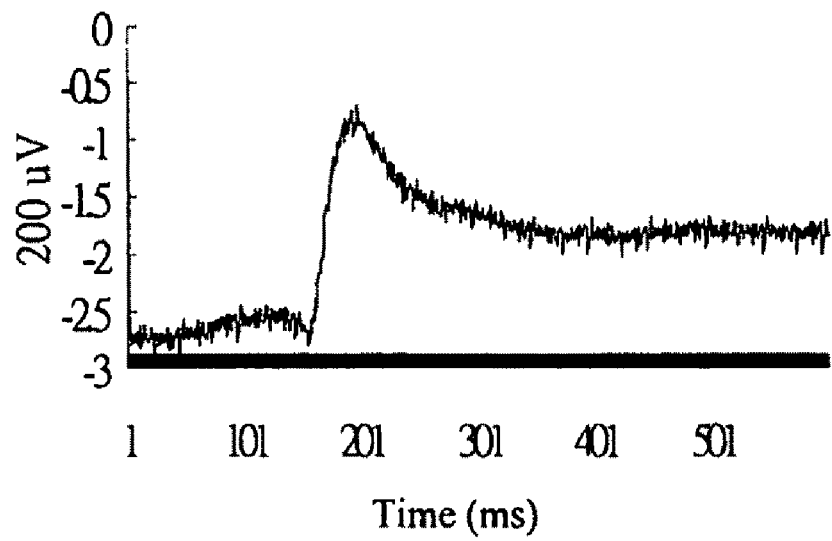
FIG. 14A is a chart showing the electro-retinograms for the mice in the DC-40 group.
Figure 14A:
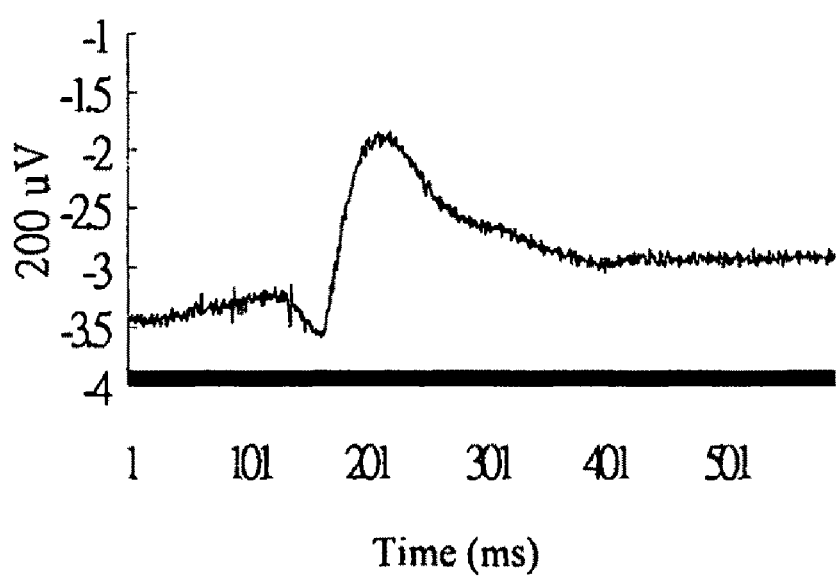
Figure 14B:
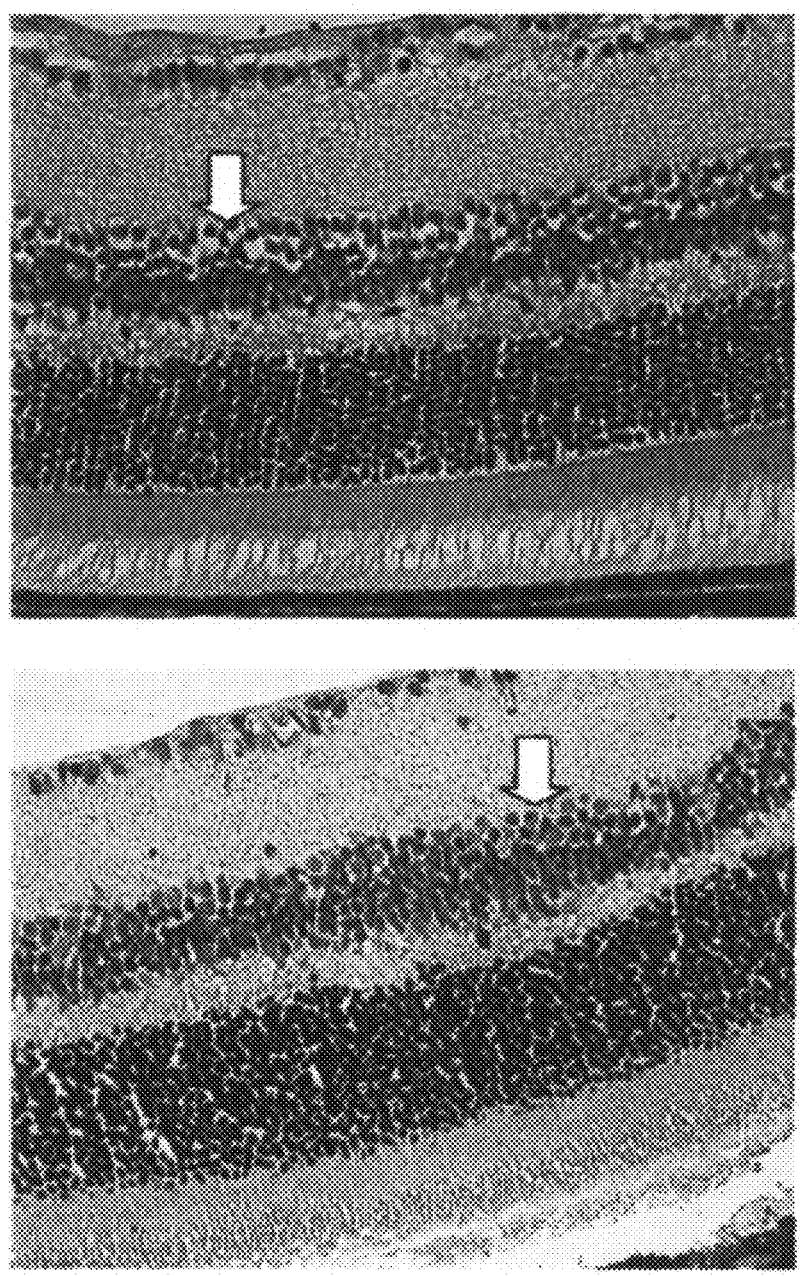
FIG. 14B is a diagram showing the histopathology of the eyes of the mice in the DC-40 group.

For the two mice randomly selected from the DC-40 group at day 28, the results of the electroretinogram analysis are respectively shown in the upper part and the lower part of FIG. 14A, wherein the flash onset was at time 100 millisecond and the flash duration was approximately 600 milliseconds. For the two mice randomly selected from the DC-40 group at day 28, the histopathology of the eyes are respectively shown in the upper part and the lower part of FIG. 14B (400× magnification). It is shown that after immunization with the IRBP peptide and oral administration of DeCaPS (40 mg/kg/day) for 28 days, the photoreceptor layer (P), the outer nuclear layer (ONL) and the inner nuclear layer (INL) of the mice in the DC-40 group are slightly damaged.

Figure 15A:
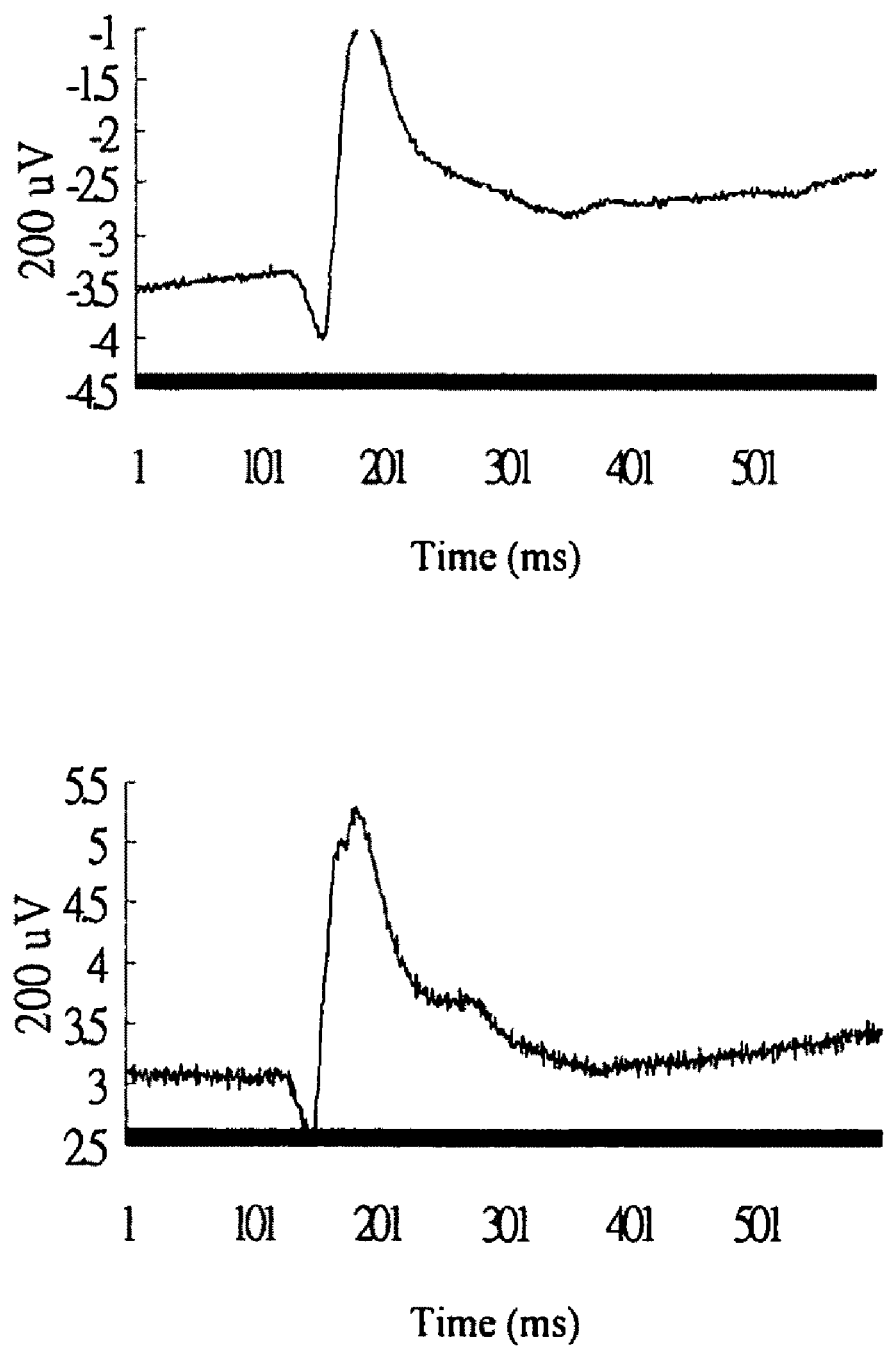
FIG. 15A is a chart showing the electro-retinograms analysis for the mice in the DC-160 group.
Figure 15B:
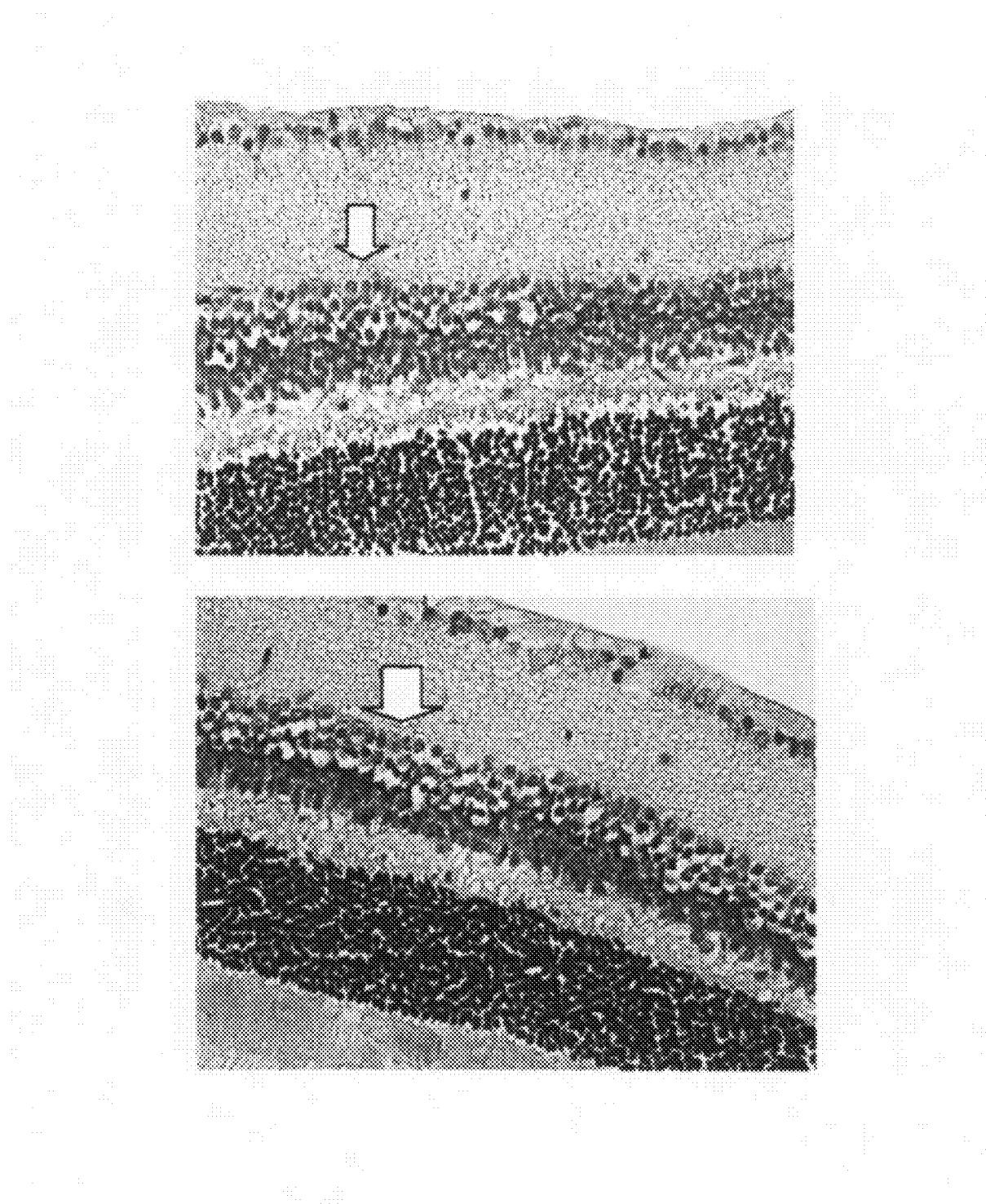
FIG. 15B is a diagram showing the histopathology of the eyes of the mice in the DC-160 group.

For the two mice randomly selected from the DC-160 group at day 28, the results of the electroretinogram analysis are respectively shown in the upper part and the lower part of FIG. 15A, wherein the flash onset was at time 100 millisecond and the flash duration was approximately 600 milliseconds. For the two mice randomly selected from the DC-160 group at day 28, the histopathology of the eyes are respectively shown in the upper part and the lower part of FIG. 15B (400× magnification). It is shown that after immunization with the IRBP peptide and oral administration of DeCaPS (160 mg/kg/day) for 28 days, the photoreceptor layer (P), the outer nuclear layer (ONL) and the inner nuclear layer (INL) of the mice in the DC-160 group are not damaged.

Accordingly, after the immunization with the IRBP peptide, it was observed that there were more cell deaths in the inner nuclear layer, but the dead cells did not sink on the outer nuclear layer. It was also observed that the cells in the inner nuclear layer were damaged by the IRBP peptide treatment, but the cell peeling off from the inner nuclear layer was significantly prevented by co-treatment with the DeCaPS at the dosage of 160 mg/kg/day.

Figure 16A:
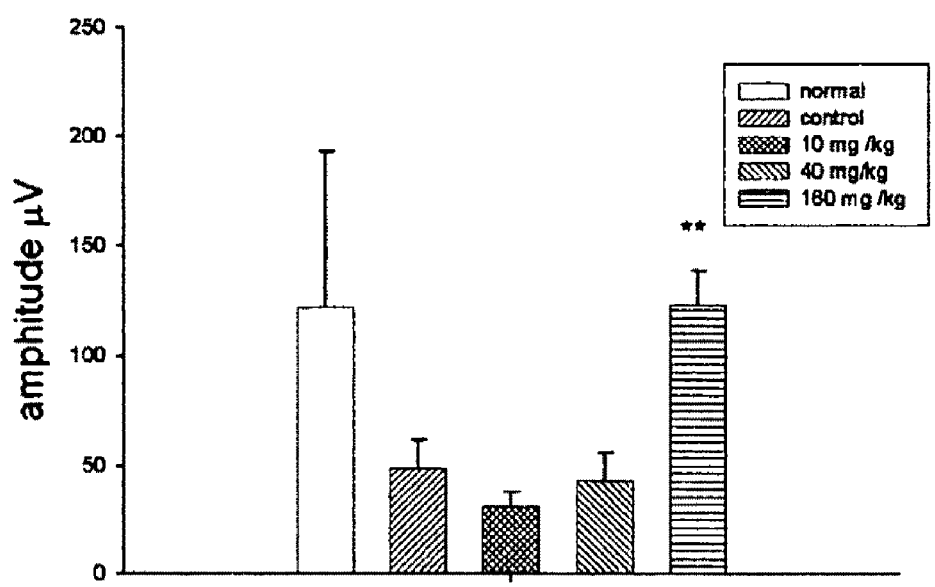
FIG. 16A is a chart showing the amplitudes of the a-waves in FIGS. 11 A, 12A, 13A, 14A and 15A.
Figure 16B:
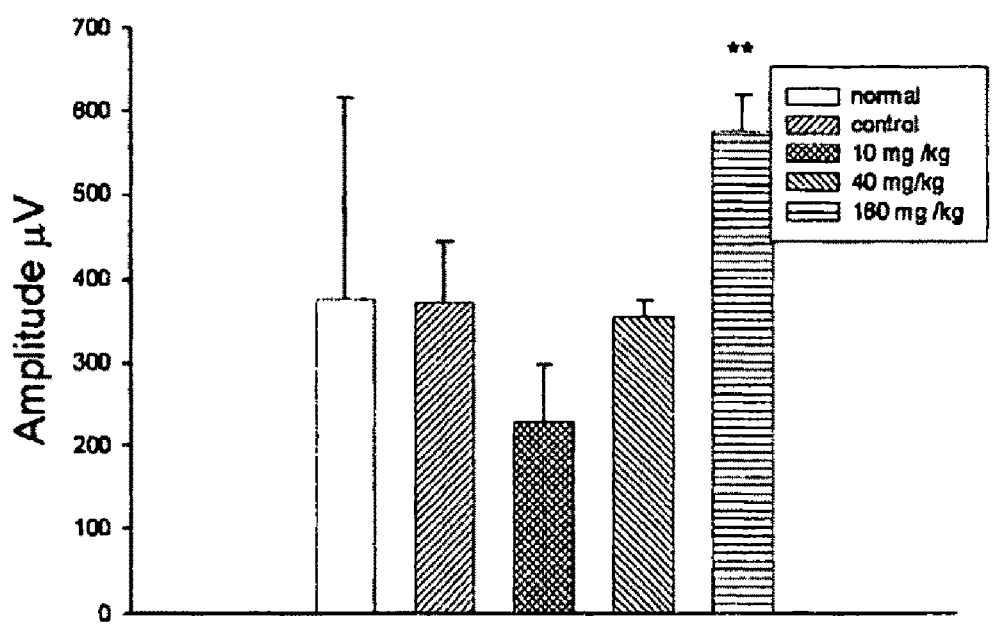
FIG. 16B is a chart showing the amplitudes of the b-waves in FIGS. 11 A, 12A, 13A, 14A and 15A.

In addition, the a-waves respectively shown in FIGS. 11A, 12A, 13A, 14A and 15A were compared in FIG. 16A (p<0.02 for the statistics), and the b-waves respectively shown in FIGS. 11A, 12A, 13A, 14A and 15A were compared in FIG. 16B (p<0.02 for the statistics). It is to be emphasized that the a-wave of the mice in the control group immunized with IRBP peptide were much lower than that of the mice in the normal group; however, with comparison to the control group, the cells peeling off from the inner nuclear layer of the mice co-treated with the DeCaPS at the dosage of 40 mg/kg/day is significantly prevented. Furthermore, the amplitudes of the a-wave and the b-wave of the mice co-treated with the DeCaPS at the dosage of 160 mg/kg/day are nearly equal to those of the mice of the normal group. It is to be further emphasized that the damage from immunization with IRBP peptide can be rescued by co-treatment with the polysaccharides, at the dosage of 160/mg/kg/day, prepared from *Dendrobium*. In other words, oral administration of polysaccharides prepared from *Dendrobium* can prevent retinal inflammation induced by IRBP.

According to the foregoing experiments, the present invention provides a composition for treating an autoimmune disease and mucosal disorder, wherein the composition includes polysaccharides prepared from *Dendrobium* and an antigen associated with induction of the autoimmune disease due to that the polysaccharides prepared from *Dendrobium* can enhance the oral tolerance induction and innate immunity promotion. Furthermore, the present invention provides a composition just including the polysaccharides prepared from *Dendrobium* for treating an autoimmune disease and mucosal disorder due to that the polysaccharides prepared from *Dendrobium* can induce the oral tolerance and promote innate immunity alone.

While the invention has been described in terms of what is presently considered to be the most practical and preferred embodiments, it is to be understood that the invention need not be limited to the disclosed embodiments. On the contrary, it is intended to cover various modifications and similar arrangements included within the spirit and scope of the appended claims which are to be accorded with the broadest interpretation so as to encompass all such modifications and similar structures.

What is claimed is:

1. A method for treating an autoimmune uveitis in a mammal in need thereof comprising:
   administering to said mammal a therapeutically effective amount of polysaccharides extracted from *Dendrobii Herba*, wherein the polysaccharides are obtained by the process comprising the following steps:
   (a) extracting the *Dendrobii Herba* with methanol to obtain a first extract;
   (b) extracting the first extract with water to obtain a second extract; and
   (c) precipitating the second extract with ethanol to obtain the polysaccharides.

2. The method according to claim 1, wherein the polysaccharides are administered orally.

* * * * *

SEQUENCE LISTING

<160> NUMBER OF SEQ ID NOS: 48

<210> SEQ ID NO 1
<211> LENGTH: 20
<212> TYPE: DNA
<213> ORGANISM: Artificial
<220> FEATURE:
<223> OTHER INFORMATION: Primer

```
<400> SEQUENCE: 1
gactacctca tgaagatcct                                              20

<210> SEQ ID NO 2
<211> LENGTH: 20
<212> TYPE: DNA
<213> ORGANISM: Artificial
<220> FEATURE:
<223> OTHER INFORMATION: Primer

<400> SEQUENCE: 2
ccacatctgc tggaaggtgg                                              20

<210> SEQ ID NO 3
<211> LENGTH: 25
<212> TYPE: DNA
<213> ORGANISM: Artificial
<220> FEATURE:
<223> OTHER INFORMATION: Primer

<400> SEQUENCE: 3
atggcaactg ttcctcaact caact                                        25

<210> SEQ ID NO 4
<211> LENGTH: 26
<212> TYPE: DNA
<213> ORGANISM: Artificial
<220> FEATURE:
<223> OTHER INFORMATION: Primer

<400> SEQUENCE: 4
caggacaggt atagattctt tcctttt                                      26

<210> SEQ ID NO 5
<211> LENGTH: 23
<212> TYPE: DNA
<213> ORGANISM: Artificial
<220> FEATURE:
<223> OTHER INFORMATION: Primer

<400> SEQUENCE: 5
atgtacagca tgcagctcgc atc                                          23

<210> SEQ ID NO 6
<211> LENGTH: 25
<212> TYPE: DNA
<213> ORGANISM: Artificial
<220> FEATURE:
<223> OTHER INFORMATION: Primer

<400> SEQUENCE: 6
ggcttgttga gatgatgctt tgaca                                        25

<210> SEQ ID NO 7
<211> LENGTH: 23
<212> TYPE: DNA
<213> ORGANISM: Artificial
<220> FEATURE:
<223> OTHER INFORMATION: Primer

<400> SEQUENCE: 7
atgggtctca accccagct agt                                           23

<210> SEQ ID NO 8
<211> LENGTH: 24
<212> TYPE: DNA
```

```
<213> ORGANISM: Artificial
<220> FEATURE:
<223> OTHER INFORMATION: Primer

<400> SEQUENCE: 8
gctctttagg ctttccagga agtc                                              24

<210> SEQ ID NO 9
<211> LENGTH: 25
<212> TYPE: DNA
<213> ORGANISM: Artificial
<220> FEATURE:
<223> OTHER INFORMATION: Primer

<400> SEQUENCE: 9
atgaagttcc tctctgcaag agact                                             25

<210> SEQ ID NO 10
<211> LENGTH: 24
<212> TYPE: DNA
<213> ORGANISM: Artificial
<220> FEATURE:
<223> OTHER INFORMATION: Primer

<400> SEQUENCE: 10
cactaggttt gccgagtaga tctc                                              24

<210> SEQ ID NO 11
<211> LENGTH: 28
<212> TYPE: DNA
<213> ORGANISM: Artificial
<220> FEATURE:
<223> OTHER INFORMATION: Primer

<400> SEQUENCE: 11
atgcaggact ttaagggtta cttgggtt                                          28

<210> SEQ ID NO 12
<211> LENGTH: 28
<212> TYPE: DNA
<213> ORGANISM: artificial
<220> FEATURE:
<223> OTHER INFORMATION: primer

<400> SEQUENCE: 12
atttcggaga gaggtacaaa cgaggttt                                          28

<210> SEQ ID NO 13
<211> LENGTH: 24
<212> TYPE: DNA
<213> ORGANISM: artificial
<220> FEATURE:
<223> OTHER INFORMATION: primer

<400> SEQUENCE: 13
aaagacaacc aactggtggt acca                                              24

<210> SEQ ID NO 14
<211> LENGTH: 24
<212> TYPE: DNA
<213> ORGANISM: artificial
<220> FEATURE:
<223> OTHER INFORMATION: primer

<400> SEQUENCE: 14
gactccgtga tgtctaagta cttg                                              24
```

<210> SEQ ID NO 15
<211> LENGTH: 24
<212> TYPE: DNA
<213> ORGANISM: artificial
<220> FEATURE:
<223> OTHER INFORMATION: primer

<400> SEQUENCE: 15
tgaacgctac acactgcatc ttgg					24

<210> SEQ ID NO 16
<211> LENGTH: 23
<212> TYPE: DNA
<213> ORGANISM: artificial
<220> FEATURE:
<223> OTHER INFORMATION: primer

<400> SEQUENCE: 16 cgactcctttt tccgcttcct gag					23

<210> SEQ ID NO 17
<211> LENGTH: 41
<212> TYPE: DNA
<213> ORGANISM: artificial
<220> FEATURE:
<223> OTHER INFORMATION: primer

<400> SEQUENCE: 17
tggaccgcaa caacgccatc tatgccatct atgagaaaac c					41

<210> SEQ ID NO 18
<211> LENGTH: 32
<212> TYPE: DNA
<213> ORGANISM: artificial
<220> FEATURE:
<223> OTHER INFORMATION: primer

<400> SEQUENCE: 18
tggagctgaa gcaatagttg gtatccaggg ct					32

<210> SEQ ID NO 19
<211> LENGTH: 20
<212> TYPE: DNA
<213> ORGANISM: artificial
<220> FEATURE:
<223> OTHER INFORMATION: primer

<400> SEQUENCE: 19
acttgtcctc ctttctgccc					20

<210> SEQ ID NO 20
<211> LENGTH: 20
<212> TYPE: DNA
<213> ORGANISM: artificial
<220> FEATURE:
<223> OTHER INFORMATION: primer

<400> SEQUENCE: 20
atccccataa tgccttctcc					20

<210> SEQ ID NO 21
<211> LENGTH: 18
<212> TYPE: DNA
<213> ORGANISM: artificial
<220> FEATURE:
<223> OTHER INFORMATION: primer

```
<400> SEQUENCE: 21
atgagcctgc gccctctg                                            18

<210> SEQ ID NO 22
<211> LENGTH: 21
<212> TYPE: DNA
<213> ORGANISM: artificial
<220> FEATURE:
<223> OTHER INFORMATION: primer

<400> SEQUENCE: 22
ggggatgctt gttagacggg a                                        21

<210> SEQ ID NO 23
<211> LENGTH: 24
<212> TYPE: DNA
<213> ORGANISM: artificial
<220> FEATURE:
<223> OTHER INFORMATION: primer

<400> SEQUENCE: 23
cctggccttc tctacaaacc ttag                                     24

<210> SEQ ID NO 24
<211> LENGTH: 22
<212> TYPE: DNA
<213> ORGANISM: artificial
<220> FEATURE:
<223> OTHER INFORMATION: primer

<400> SEQUENCE: 24
agatcaacag gagaagggca ca                                       22

<210> SEQ ID NO 25
<211> LENGTH: 22
<212> TYPE: DNA
<213> ORGANISM: artificial
<220> FEATURE:
<223> OTHER INFORMATION: primer

<400> SEQUENCE: 25
ttgaagacaa ggcatggcat gg                                       22

<210> SEQ ID NO 26
<211> LENGTH: 20
<212> TYPE: DNA
<213> ORGANISM: artificial
<220> FEATURE:
<223> OTHER INFORMATION: primer

<400> SEQUENCE: 26
tctcccaaga tcaaccgatg                                          20

<210> SEQ ID NO 27
<211> LENGTH: 25
<212> TYPE: DNA
<213> ORGANISM: artificial
<220> FEATURE:
<223> OTHER INFORMATION: primer

<400> SEQUENCE: 27
gcttcgtgtt ttggacataa ctcat                                    25

<210> SEQ ID NO 28
<211> LENGTH: 21
<212> TYPE: DNA
```

```
<213> ORGANISM: artificial
<220> FEATURE:
<223> OTHER INFORMATION: primer

<400> SEQUENCE: 28
gcggtcttca ggccacctca a                                              21

<210> SEQ ID NO 29
<211> LENGTH: 21
<212> TYPE: DNA
<213> ORGANISM: artificial
<220> FEATURE:
<223> OTHER INFORMATION: primer

<400> SEQUENCE: 29
gctgtgtggt ttgtctggtg g                                              21

<210> SEQ ID NO 30
<211> LENGTH: 20
<212> TYPE: DNA
<213> ORGANISM: artificial
<220> FEATURE:
<223> OTHER INFORMATION: primer

<400> SEQUENCE: 30
cagggcattt ttcaggcact                                                20

<210> SEQ ID NO 31
<211> LENGTH: 18
<212> TYPE: DNA
<213> ORGANISM: artificial
<220> FEATURE:
<223> OTHER INFORMATION: primer

<400> SEQUENCE: 31
tatcctccgg ccccagaa                                                  18

<210> SEQ ID NO 32
<211> LENGTH: 21
<212> TYPE: DNA
<213> ORGANISM: artificial
<220> FEATURE:
<223> OTHER INFORMATION: primer

<400> SEQUENCE: 32
caactgcgct ctgtgcctta t                                              21

<210> SEQ ID NO 33
<211> LENGTH: 1619
<212> TYPE: DNA
<213> ORGANISM: Mus musculus

<400> SEQUENCE: 33
cctcagcgag acagcaagg gactagccag gagggagaac agaaactcca gaacatcttg      60
gaaatagctc ccagaaaagc aagcagccaa ccaggcaggt tctgtccctt tcactcactg    120
gcccaaggcg ccacatctcc ctccagaaaa gacaccatga gcacagaaag catgatccgc    180
gacgtggaac tggcagaaga ggcactcccc caaaagatgg ggggcttcca gaactccagg    240
cggtgcctat gtctcagcct cttctcattc ctgcttgtgg caggggccac cacgctcttc    300
tgtctactga acttcggggt gatcggtccc caaagggatg agaagttccc aaatggcctc    360
cctctcatca gttctatggc ccagacccct cacactcagat catcttctca aaattcgagt    420
gacaagcctg tagcccacgt cgtagcaaac caccaagtgg aggagcagct ggagtggctg    480
```

```
agccagcgcg ccaacgccct cctggccaac ggcatggatc tcaaagacaa ccaactagtg      540
gtgccagccg atgggttgta ccttgtctac tcccaggttc tcttcaaggg acaaggctgc      600
cccgactacg tgctcctcac ccacaccgtc agccgatttg ctatctcata ccaggagaaa      660
gtcaacctcc tctctgccgt caagagcccc tgccccaagg acacccctga gggggctgag      720
ctcaaaccct ggtatgagcc catatacctg ggaggagtct tccagctgga aggggggac      780 caactcagcg ctgaggtcaa tctgcccaag tacttagact ttgcggagtc cgggcaggtc      840
tactttggag tcattgctct gtgaagggaa tgggtgttca tccattctct acccagcccc      900
cactctgacc cctttactct gaccccttta ttgtctactc ctcagagccc ccagtctgtg      960
tccttctaac ttagaaaggg gattatggct cagagtccaa ctctgtgctc agagctttca     1020
acaactactc agaaacacaa gatgctggga cagtgacctg gactgtgggc ctctcatgca     1080
ccaccatcaa ggactcaaat gggctttccg aattcactgg agcctcgaat gtccattcct     1140
gagttctgca agggagagt ggtcaggttg cctctgtctc agaatgaggc tggataagat     1200
ctcaggcctt cctaccttca gacctttcca gactcttccc tgaggtgcaa tgcacagcct     1260
tcctcacaga gccagccccc ctctatttat atttgcactt attatttatt atttatttat     1320
tatttattta tttgcttatg aatgtattta tttggaaggc cggggtgtcc tggaggaccc     1380
agtgtgggaa gctgtcttca gacagacatg ttttctgtga aaacggagct gagctgtccc     1440
cacctggcct ctctaccttg ttgcctcctc ttttgcttat gtttaaaaca aaatatttat     1500
ctaacccaat tgtcttaata acgctgattt ggtgaccagg ctgtcgctac atcactgaac     1560
ctctgctccc cacgggagcc gtgactgtaa ttgccctaca gtcaattgag agaaataaa      1619

<210> SEQ ID NO 34
<211> LENGTH: 1314
<212> TYPE: DNA
<213> ORGANISM: Mus musculus

<400> SEQUENCE: 34
gggggggggg atttagagac ttgctcttgc actaccaaag ccacaaagca gccttgcaga       60
aaagagagct ccatcatgcc tggctcagca ctgctatgct gcctgctctt actgactggc      120
atgaggatca gcagggggcca gtacagccgg gaagacaata actgcaccca cttcccagtc      180
ggccagagcc acatgctcct agagctgcgg actgccttca gccaggtgaa gactttcttt      240
caaacaaagg accagctgga caacatactg ctaaccgact ccttaatgca ggactttaag      300
ggttacttgg gttgccaagc cttatcgaa atgatccagt tttacctggt agaagtgatg      360
ccccaggcag agaagcatgg cccagaaatc aaggagcatt tgaattccct gggtgagaag      420
ctgaagaccc tcaggatgcg gctgaggcgc tgtcatcgat ttctcccctg tgaaaataag      480
agcaaggcag tggagcaggt gaagagtgat tttaataagc tccaagacca aggtgtctac      540
aaggccatga atgaatttga catcttcatc aactgcatag aagcatacat gatgatcaaa      600
atgaaaagct aaaacacctg cagtgtgtat tgagtctgct ggactccagg acctagacag      660
agctctctaa atctgatcca gggatcttag ctaacgaaa caactccttg gaaacctcg       720 tttgtacctc tctccgaaat atttattacc tctgatacct cagttcccat tctatttatt      780
cactgagctt ctctgtgaac tatttagaaa gaagcccaat attataattt tacagtattt      840
attattttta acctgtgttt aagctgtttc cattgggac actttatagt atttaagg       900 agattatatt atatgatggg aggggttctt ccttgggaag caattgaagc ttctattcta      960
aggctggcca cacttgagag ctgcagggcc ctttgctatg gtgtcctttc aattgctctc     1020
```

| atccctgagt tcagagctcc taagagagtt gtgaagaaac tcatgggtct tgggaagaga | 1080 |
| aaccagggag atcctttgat gatcattcct gcagcagctc agagggttcc cctactgtca | 1140 |
| tcccccagcc gcttcatccc tgaaaactgt ggccagtttg ttatttataa ccacctaaaa | 1200 |
| ttagttctaa tagaactcat ttttaactag aagtaatgca attcctctgg gaatggtgta | 1260 |
| ttgtttgtct gcctttgtag cagcatctaa ttttgaataa atggatctta ttcg | 1314 |

<210> SEQ ID NO 35
<211> LENGTH: 470
<212> TYPE: DNA
<213> ORGANISM: Mus musculus

<400> SEQUENCE: 35

| tgaatcttcc aggtgactcc cagccatgaa gacactagtc ctcctctctg ccctcgtcct | 60 |
| gccttgcttc caggtccagg ctgatcctat ccaaaacaca gatgaagaga ctaaaactga | 120 |
| ggagcagcca gaggaagagg accaggctgt ttctgtctcc tttggaggca cagaaggctc | 180 |
| tgctcttcaa gatgtagccc aaagaaggtt ccgtggtgc cggaagtgcc gagtgtgcca | 240 |
| gaagtgccaa gtgtgccaga agtgcccgt gtgcccgaca tgcccccagt gcccaaagca | 300 |
| gccattgtgc gaagaaaggc aaaataaaac tgcaatcacc acccaagctc caaatacaca | 360 |
| gcataaaggc tgttgagctg aatgtggaat ctggttgag atgaccattt gcttttggtc | 420 |
| ctcacgatcc cgttgtgctt agcgtcaatt gcaattcctt ctctcataaa | 470 |

<210> SEQ ID NO 36
<211> LENGTH: 722
<212> TYPE: DNA
<213> ORGANISM: Mus musculus

<400> SEQUENCE: 36

| gagcttgaca ccgaaggacc ctgtctccag gagcacacag ctagactcgt ccccagttgg | 60 |
| aggaaagctg gccagctttg gaatcactgt tggaagagat gacaatgagc ccatgtcctt | 120 |
| tgttgttggt cttcgtgctg ggtctggttg tgattcctcc aactctggct cagaatgaaa | 180 |
| ggtacgaaaa attcctacgt cagcactatg atgccaagcc aaagggccgg gacgacagat | 240 |
| actgtgaaag tatgatgaag gaaagaaagc taacctcgcc ttgcaaagat gtcaacacct | 300 |
| ttatccatgg caccaagaaa aacatcaggg ccatctgtgg aaagaaagga agcccttatg | 360 |
| gagaaaactt cagaataagc aattctccct tccagatcac cacttgtacg cactcaagag | 420 |
| ggtctccctg gcctccatgc gggtaccgag cctttaaaga tttcagatat attgttattg | 480 |
| cctgtgaaga tggctggcct gtccacttcg atgagtcttt tatcagtccg tagacagcag | 540 |
| gcccctggca cagacctagg tctgtttct ttttatctcc cctcacagcc atgatcactg | 600 |
| gttcaccgtt cactgtcacg ggccagaaaa tgaattatct gaaatatact ctcctcatt | 660 |
| tataatgcac agaaataaag atatctcaaa amccataaaa aaaaaaaaa aaaaaaaaa | 720 |
| aa | 722 |

<210> SEQ ID NO 37
<211> LENGTH: 3046
<212> TYPE: DNA
<213> ORGANISM: Mus musculus

<400> SEQUENCE: 37

| cggagcctct ggactttcag ttctgttttg cctgccctgt ggctcctgcc agctctgatg | 60 |
| ccaggctccg ttcccttgc agacccctgt gggcggcgct tgccgcaccg ggggcggtgc | 120 |

```
tggcgaccgg gaagttcggg gccctgacct ggggacatcc ccttccctca cttccaggtc    180
ttcagtcttc ctaggctggt gcccagatgg ctagtgggca cggggagcgg cggctggagg    240
actcctaggc tccgggcagg cggtcactgg caggagatgt gtccgcaatc atagtttctg    300
atggtgaagg ttgacggca gtctctgcga cctagaagtg aaaagatgt cgttcaagga     360 ggtgcggact gtttccttct gaccaggatc ttgtttctga gtgtaggggc ttcacttctc    420
tgcttttcgt tcatctctgg agcatccgaa ttgcatcacc ggtcagaaaa caacttaccg    480
aaacctcaga caaagcgtca atctcagag gatgctacga gctctttggc tcttctggat     540
cttggtggcc ataacagtcc tcttcagcaa acgctgttct gctcaggagt ctctgtcatg    600
tgatgcttct ggggtgtgtg atggccgctc caggtctttc acctctattc cctccggact    660
cacagcagcc atgaaaagcc ttgacctgtc tttcaacaag atcacctaca ttggccatgg    720
tgacctccga gcgtgtgcga acctccaggt tctgatttg aagtccagca gaatcaatac    780
aatagaggga gacgcctttt attctctggg cagtcttgaa catttggatt tgtctgataa    840
tcacctatct agtttatctt cctcctggtt cgggcccctt tcctctttga aatacttaaa    900
cttaatggga aatccttacc agacactggg ggtaacatcg cttttcccca atctcacaaa    960
tttacaaacc ctcaggatag gaaatgtaga gactttcagt gagataagga gaatagattt   1020
tgctgggctg acttctctca atgaacttga aattaaggca ttaagtctcc ggaattatca   1080
gtcccaaagt ctaaagtcga tccgcgacat ccatcacctg actcttcact taagcgagtc   1140
tgctttcctg ctggagattt ttgcagatat tctgagttct gtgagatatt tagaactaag   1200
agatactaac ttggccaggt tccagttttc accactgccc gtagatgaag tcagctcacc   1260
gatgaagaag ctggcattcc gaggctcggt tctcactgat gaaagcttta acgagctcct   1320
gaagctgttg cgttacatct tggaactgtc ggaggtagag ttcgacgact gtaccctcaa   1380
tgggctcggc gatttcaacc cctcggagtc agacgtagtg agcgagctgg gtaaagtaga   1440
aacagtcact atccggaggt tgcatatccc ccagttctat ttgttttatg acctgagtac   1500
tgtctattcc ctcctggaga aggtgaagcg aatcacagta gagaacagca aggtcttcct   1560
ggttccctgc tcgttctccc agcatttaaa atcattagaa ttcttagacc tcagcgaaaa   1620
tctgatggtt gaagaatatt tgaagaactc agcctgtaag ggagcctggc ctcctctaca   1680
aaccttagtt ttgagccaga atcatttgag atcaatgcaa aaaacaggag agattttgct   1740
gactctgaaa aacctgacct cccttgacat cagcaggaac acttttcatc gatgcccga    1800 cagctgtcag tggccagaaa agatgcgctt cctgaatttg tccagtacag ggatccgggt   1860
ggtaaaaacg tgcattcctc agacgctgga ggtgttggat gttagtaaca caatcttga    1920 ctcatttcct ttgttcttgc ctcggctgca agagctctat attccagaa ataagctgaa    1980 aacactccca gatgcttcgt tgttccctgt gttgctggtc atgaaaatca gagagaatgc   2040
agtaagtact ttctctaaag accaacttgg ttcttttccc aaactggaga ctctggaagc   2100
aggcgacaac cactttgttt gctcctgcga actcctatcc tttactatgg agacgccagc   2160
tctggctcaa atcctggttg actggccaga cagctacctg tgtgactctc cgcctcgcct   2220
gcacggccac aggcttcagg atgcccggcc ctccgtcttg aatgtcacc aggctgcact    2280 ggtgtctgga gtctgctgtg cccttctcct gttgatcttg ctcgtaggtg ccctgtgcca   2340
ccatttccac gggctgtggt acctgagaat gatgtgggcg tggctccagg ccaagaggaa   2400
gcccaagaaa gctccctgca gggacgtttg ctatgatgcc tttgtttcct acagtgagca   2460
ggattcccat tgggtggaga acctcatggt ccagcagctg gagaactctg acccgcctt    2520
```

-continued

| | | | | |
|---|---|---|---|---|
| taagctgtgt | ctccacaagc | gggacttcgt | tccgggcaaa | tggatcattg acaacatcat | 2580 |
| cgattccatc | gaaaagagcc | acaaaactgt | gttcgtgctt | tctgagaact tcgtacggag | 2640 |
| cgagtggtgc | aagtacgaac | tggacttctc | ccacttcagg | ctctttgacg agaacaacga | 2700 |
| cgcggccatc | cttgttttgc | tggagcccat | tgagaggaaa | gccattcccc agcgcttctg | 2760 |
| caaactgcgc | aagataatga | acaccaagac | ctacctggag | tggcccttgg atgaaggcca | 2820 |
| gcaggaagtg | ttttgggtaa | atctgagaac | tgcaataaag | tcctaggttc tccacccagt | 2880 |
| tcctgacttc | cttaactaag | gtctttgtga | cacaaactgt | aacaaagttt ataagtaaca | 2940 |
| tagaattgta | ttattgagga | tattaactat | gggttttgtc | ttgaatactg ttatataaat | 3000 |
| atgtgacatc | aggaaaaaaa | aaaaaaaaaa | aaaaaaaaaa | aaaaaa | 3046 |

<210> SEQ ID NO 38
<211> LENGTH: 3866
<212> TYPE: DNA
<213> ORGANISM: Mus musculus

<400> SEQUENCE: 38

| | | | | |
|---|---|---|---|---|
| ctggttgcag | aaaatgccag | gatgatgcct | ccctggctcc | tggctaggac tctgatcatg | 60 |
| gcactgttct | tctcctgcct | gacaccagga | agcttgaatc | cctgcataga ggtagttcct | 120 |
| aatattacct | accaatgcat | ggatcagaaa | ctcagcaaag | tccctgatga cattccttct | 180 |
| tcaaccaaga | acatagatct | gagcttcaac | cccttgaaga | tcttaaaaag ctatagcttc | 240 |
| tccaattttt | cagaacttca | gtggctggat | ttatccaggt | gtgaaattga acaattgaa | 300 |
| gacaaggcat | ggcatggctt | acaccacctc | tcaaacttga | tactgacagg aaaccctatc | 360 |
| cagagttttt | ccccaggaag | tttctctgga | ctaacaagtt | tagagaatct ggtggctgtg | 420 |
| gagacaaaat | tggcctctct | agaaagcttc | cctattggac | agcttataac cttaaagaaa | 480 |
| ctcaatgtgg | ctcacaattt | tatacattcc | tgtaagttac | ctgcatattt ttccaatctg | 540 |
| acgaacctag | tacatgtgga | tctttcttat | aactatattc | aaactattac tgtcaacgac | 600 |
| ttacagtttc | tacgtgaaaa | tccacaagtc | aatctctctt | tagacatgtc tttgaaccca | 660 |
| attgacttca | ttcaagacca | agcctttcag | ggaattaagc | tccatgaact gactctaaga | 720 |
| ggtaattttta | atagctcaaa | tataatgaaa | acttgccttc | aaaacctggc tggtttacac | 780 |
| gtccatcggt | tgatcttggg | agaatttaaa | gatgaaagga | atctgaaaat ttttgaaccc | 840 |
| tctatcatgg | aaggactatg | tgatgtgacc | attgatgagt | tcaggttaac atatacaaat | 900 |
| gattttttcag | atgatattgt | taagttccat | tgcttggcga | atgtttctgc aatgtctctg | 960 |
| gcaggtgtat | ctataaaata | tctagaagat | gttcctaaac | atttcaaatg gcaatcctta | 1020 |
| tcaatcatta | gatgtcaact | taagcagttt | ccaactctgg | atctacccctt tcttaaaagt | 1080 |
| ttgactttaa | ctatgaacaa | agggtctatc | agttttaaaa | aagtggccct accaagtctc | 1140 |
| agctatctag | atcttagtag | aaatgcactg | agctttagtg | ttgctgttc ttattctgat | 1200 |
| ttgggaacaa | acagcctgag | acacttagac | ctcagcttca | atggtgccat cattatgagt | 1260 |
| gccaatttca | tgggtctaga | agagctgcag | cacctggatt | tcagcactc tactttaaaa | 1320 |
| agggtcacag | aattctcagc | gttcttatcc | cttgaaaagc | tactttacct tgacatctct | 1380 |
| tatactaaca | ccaaaattga | cttcgatggt | atatttcttg | gcttgaccag tctcaacaca | 1440 |
| ttaaaaatgg | ctggcaattc | tttcaaagac | aacacccttt | caaatgtctt tgcaaacaca | 1500 |
| acaaacttga | cattcctgga | tctttctaaa | tgtcaattgg | aacaaatatc ttgggggggta | 1560 |
| tttgacaccc | tccatagact | tcaattatta | aatatgagtc | acaacaatct attgttttttg | 1620 |

```
gattcatccc attataacca gctgtattcc ctcagcactc ttgattgcag tttcaatcgc    1680
atagagacat ctaaaggaat actgcaacat tttccaaaga gtctagcctt cttcaatctt    1740
actaacaatt ctgttgcttg tatatgtgaa catcagaaat tcctgcagtg ggtcaaggaa    1800
cagaagcagt tcttggtgaa tgttaacaa atgacatgtg caacacctgt agagatgaat    1860
acctccttag tgttggattt taataattct acctgttata tgtacaagac aatcatcagt    1920
gtgtcagtgg tcagtgtgat tgtggtatcc actgtagcat ttctgatata ccacttctat    1980
tttcacctga tacttattgc tggctgtaaa aagtacagca gaggagaaag catctatgat    2040
gcatttgtga tctactcgag tcagaatgag actgggtga gaaatgagct ggtaaagaat    2100
ttagaagaag gagtgccccg cttttcacctc tgccttcact acagagactt tattcctggt    2160
gtagccattg ctgccaacat catccaggaa ggcttccaca agagccggaa ggttattgtg    2220
gtagtgtcta gacactttat tcagagccgt tggtgtatct ttgaatatga gattgctcaa    2280
acatggcagt ttctgagcag ccgctctggc atcatcttca ttgtccttga aaggttgag    2340 aagtccctgc tgaggcagca ggtggaattg tatcgccttc ttagcagaaa cacctacctg    2400
gaatgggagg acaatcctct ggggaggcac atcttctgga gaagacttaa aaatgcccta    2460
ttggatggaa aagcctcgaa tcctgagcaa acagcagagg aagaacaaga acggcaact    2520 tggacctgag gagaacaaaa ctctgggggcc taaacccagt ctgtttgcaa ttaataatg    2580 ctacagctca cctggggctc tgctatggac cgagagccca tggaacacat ggctgctaag    2640
ctatagcatg gaccttaccg ggcagaagga agtagcactg acaccttcct ttccaggggt    2700
atgaattacc taactcggga aagaaacat aatccagaat ctttaccttt aatctgaagg    2760
agaagaggct aaggcctagt gagaacagaa aggagaacca gtcttcactg gccttttga    2820 atacaagcca tgtcatgttc tgtgtttcag ttgctttaga agagtattga tagtttcaac    2880
tgaactgaac ggtttcttac ttttccctttt ttctactgaa tgcaatatta aatagctctt    2940
tttgagaggt cttcattcca atttcatctt ccatttttatg tcattttctt ttctttttg    3000 tttttatcta attctataag aaatatgatt gatacacgct cacagatagc ctggccaatc    3060
ctaagaatgc tatatttatt aaatacaatt cctagtatac ttttacttt ataaattcag    3120 ttatcgttttt tcatgccttg actataaact aatatcataa ataagattgt tacaggtatg    3180
ctaagaaggc ccatatttga ctataatttt ttaagaaagt atataaaata ctttgtca    3240 tattgtcact gaatgtcatt cttaagttat tacctaagtt atggatgtca cagagtcagt    3300
gttaaaaata atttggttga tagaaatatt tttaatcagg agggaaaagt ggagagggt    3360 gcaggaacag aaatcatgat ttcatcattt attcttgatt ttttccggaag ttcacatagc    3420 tgaatgacaa gactacatat gctgcaactg atgttccttc tcatcaagga tactctctga    3480
acttgagaac attttgggga ggaagaaagg tctaacatcc ttttccttca tcattctcat    3540
ttctggacat gccttgtgag atggatcaat gttgggagta cacatttctg ctttcacctt    3600
atttcagtca gcatgaacac tgaatatata atgtcatttc acagtgtgtg tgtgttgtgt    3660
atgtacatat atgaacctgt acatgtgttt aagtttaaag agaaaatagt gtacagagca    3720
ggtgtatatt tgtgatagg cttttaaatag ttgagctaat tcagaaaagt atggaggttt    3780
cttggtaaac caaccaaaa gtagaatcat tacaagatct aacaataaaa attttgaaaa    3840
aaaaaaaaaa aaaaaaaaaa aaaaaa                                         3866
```

<210> SEQ ID NO 39
<211> LENGTH: 2625
<212> TYPE: DNA

<213> ORGANISM: Mus musculus

<400> SEQUENCE: 39

```
aagaggtaat ccgaaggaag tcttggtaag taagaaggct tttctggatt tttcaaatta        60
ctgcgttgat atttcaatcg agaaagaaaa tggtaccgtc agtgctggaa atagagcttg       120
gatccaagta aaaatgctgt gaagaatggt aaagtccctc tgggatagcc tctgcaacat       180
gagccaagac agaaaaccca tcgtggggag tttccacttt gtttgcgccc tggccttaat       240
agtcggaagc atgaccccgt tctctaatga acttgagtct atggtagact attcaaacag       300
gaaccttact catgtcccca agacctgcc accaagaaca aaagccctga gtctgtctca        360
aaactctata tctgagcttc ggatgcctga tatcagcttt ctgtcagagc tgagagttct       420
gagactctcc cacaacagga tacgagcct tgatttccat gtattcttgt tcaatcagga        480
cttagaatac ctggatgtct cacacaatcg gttgcaaaac atctcttgct gccctatggc       540
gagcctgagg catctagacc tctcattcaa tgactttgat gtactgcctg tgtgtaagga       600
atttggcaac ctgacgaagc tgactttcct gggattaagt gctgcaaagt tccgacaact       660
ggatctgctc ccagttgctc acttgcatct aagctgcatt cttctggact tagtgagtta       720
tcatataaaa ggcggggaaa cagaaagtct tcagattccc aataccaccg ttctccattt       780
ggtcttttcat ccaaatagct tgttctctgt tcaagtgaac atgtctgtaa acgctttagg     840
acatttacaa ctgagtaata ttaaattgaa tgatgaaaac tgtcaaaggt taatgacatt       900
tttatcagaa ctcaccagag gtccaaccctt attgaatgtg accctccagc acatagaaac     960
aacctggaag tgctcggtta acttttccca attcttttgg ccccgaccgg tggagtacct      1020
caatatttac aacttaacga taactgagag aatcgacagg gaagaattta cttactcgga      1080
gacagcactg aagtcactga tgatagagca cgtcaaaaac caagtgttcc tcttttcaaa      1140
ggaggcgcta tactcggtgt ttgctgagat gaacatcaag atgctctcta tctcagacac      1200
ccctttcatc cacatggtgt gcccgccatc cccaagctca tttacatttc tgaactttac      1260
ccagaatgtt tttactgaca gtgttttttca aggctgttcc accttaaaga gattgcagac     1320
acttatctta caaggaatg gtttgaagaa cttttttaaa gtagctctca tgactaagaa       1380
tatgtcctct ctggaaactt tggatgttag tttgaattct ttgaactctc atgcatatga      1440
caggacatgc gcctgggctg agagcatatt ggtgttgaat ttgtcttcga atatgcttac      1500
aggctctgtc ttcagatgct tacctcccaa ggtcaaggtc cttgaccttc acaacaacag      1560
gataatgagc atccctaaag atgtcaccca cctgcaggct ttgcaggaac tcaatgtagc      1620
atccaactcc ttaactgacc ttcctgggtg tggggccttc agcagccttt ctgtgctggt      1680
catcgaccat aactcagttt cccatccctc tgaggatttc ttccagagct gtcagaatat      1740
tagatcccta acagcgggaa acaacccatt ccaatgcaca tgtgagctga gggactttgt      1800
caagaacata ggctgggtag caagagaagt ggtggagggc tggcctgact cttacaggtg      1860
tgactaccca gaaagctcta agggaactgc actgagggac ttccacatgt ctccactgtc      1920
ctgtgatact gttctgctga ctatcaccat cggggccact atgctggtgc tggctgtcac      1980
tggggctttc ctctgtctct actttgacct gccctggtat gtgaggatgc tgtgtcagtg      2040
gacacagacc aggcacaggg ccaggcacat ccccttagag gaactccaga gaaacctcca      2100
gttccatgct tttgtctcat acagtgagca tgattctgcc tgggtgaaga acgaattact      2160
acccaaccta gagaaagatg acatccgggt ttgcctccat gagaggaact ttgtccctgg      2220
caagagcatt gtggagaaca tcatcaattt cattgagaag agttacaagg ccatcttgt       2280
```

-continued

| | |
|---|---|
| gctgtctccc cacttcatcc agagtgagtg gtgccattat gaactctatt ttgcccatca | 2340 |
| taatctcttc catgaaggct ctgataactt aatcctcatc ttgctggaac ccattctaca | 2400 |
| gaacaacatt cccagtagat accacaagct gcgggctctc atggcacagc ggacttactt | 2460 |
| ggaatggcct actgagaagg gcaaacgtgg gctgttttgg gccaaccttaa gagcttcatt | 2520 |
| tattatgaag ttagccttag tcaatgagga tgatgtgaaa acttgaaact tgggtttcta | 2580 |
| acttaataaa ctgtcaacct ggaaaaaaaa aaaaaaaaa aaaaa | 2625 |

<210> SEQ ID NO 40
<211> LENGTH: 3471
<212> TYPE: DNA
<213> ORGANISM: Mus musculus

<400> SEQUENCE: 40

| | |
|---|---|
| tgaaagtgtc acttcctcaa ttctctgaga daccctggtg tggaacatca ttctctgccg | 60 |
| cccagtttgt cagagggagc ctcgggagaa tcctccatct cccaacatgg ttctccgtcg | 120 |
| aaggactctg caccccttgt ccctcctggt acaggctgca gtgctggctg agactctggc | 180 |
| cctgggtacc ctgcctgcct tcctaccctg tgagctgaag cctcatggcc tggtggactg | 240 |
| caattggctg ttcctgaagt ctgtaccccg tttctctgcg gcagcatcct gctccaacat | 300 |
| cacccgcctc tccttgatct ccaaccgtat ccaccacctg cacaactccg acttcgtcca | 360 |
| cctgtccaac ctgcggcagc tgaacctcaa gtggaactgt ccacccactg gccttagccc | 420 |
| cctgcacttc tcttgccaca tgaccattga gcccagaacc ttcctggcta tgcgtacact | 480 |
| ggaggagctg aacctgagct ataatggtat caccactgtg ccccgactgc ccagctccct | 540 |
| ggtgaatctg agcctgagcc acaccaacat cctggttcta gatgctaaca gcctcgccgg | 600 |
| cctatacagc ctgcgcgttc tcttcatgga cgggaactgc tactacaaga accctgcac | 660 |
| aggagcggtg aaggtgaccc caggcgcccct cctgggcctg agcaatctca cccatctgtc | 720 |
| tctgaagtat aacaacctca caaaggtgcc ccgccaactg ccccccagcc tggagtacct | 780 |
| cctggtgtcc tataacctca ttgtcaagct ggggcctgaa gacctggcca atctgacctc | 840 |
| ccttcgagta cttgatgtgg gtgggaattg ccgtcgctgc gaccatgccc caatccctg | 900 |
| tatagaatgt ggccaaaagt ccctccacct gcaccctgag accttccatc acctgagcca | 960 |
| tctggaaggc ctggtgctga aggacagctc tctccataca ctgaactctt cctggttcca | 1020 |
| aggtctggtc aacctctcgg tgctggacct aagcgagaac tttctctatg aaagcatcaa | 1080 |
| ccacaccaat gcctttcaga acctaaaccg ctgcgcaag ctcaacctgt ccttcaatta | 1140 |
| ccgcaagaag gtatcctttg cccgcctcca cctggcaagt tccttcaaga acctggtgtc | 1200 |
| actgcaggag ctgaacatga acggcatctt cttccgctcg ctcaacaagt acacgctcag | 1260 |
| atggctggcc gatctgccca aactccacac tctgcatctt caaatgaact tcatcaacca | 1320 |
| ggcacagctc agcatctttg gtaccttccg agcccttcgc tttgtggact tgtcagacaa | 1380 |
| tcgcatcagt gggccttcaa cgctgtcaga agccaccct gaagaggcag atgatgcaga | 1440 |
| gcaggaggag ctgttgtctg cggatcctca cccagctcca ctgagcaccc ctgcttctaa | 1500 |
| gaacttcatg gacaggtgta agaacttcaa gttcaccatg gacctgtctc ggaacaacct | 1560 |
| ggtgactatc aagccagaga tgtttgtcaa tctctcacgc ctccagtgtc ttagcctgag | 1620 |
| ccacaactcc attgcacagg ctgtcaatgg ctctcagttc ctgccgctga ctaatctgca | 1680 |
| ggtgctggac ctgtcccata caaaactgga cttgtaccac tggaaatcgt tcagtgagct | 1740 |
| accacagttg caggccctgg acctgagcta caacagccag ccctttagca tgaagggtat | 1800 |

```
aggccacaat ttcagttttg tgacccatct gtccatgcta cagagcctta gcctggcaca   1860
caatgacatt catacccgtg tgtcctcaca tctcaacagc aactcagtga ggtttcttga   1920
cttcagcggc aacggtatgg gccgcatgtg ggatgagggg ggcctttatc tccatttctt   1980
ccaaggcctg agtggcctgc tgaagctgga cctgtctcaa ataacctgc atatcctccg    2040
gccccagaac cttgacaacc tccccaagag cctgaagctg ctgagcctcc gagacaacta   2100
cctatctttc tttaactgga ccagtctgtc cttcctaccc aacctggaag tcctagacct   2160
ggcaggcaac cagctaaagg ccctgaccaa tggcaccctg cctaatggca ccctcctcca   2220
gaaactcgat gtcagtagca acagtatcgt ctctgtggtc ccagccttct tcgctctggc   2280
ggtcgagctg aaagaggtca acctcagcca caacattctc aagacggtgg atcgctcctg   2340
gtttgggccc attgtgatga acctgacagt tctagacgtg agaagcaacc ctctgcactg   2400
tgcctgtggg gcagccttcg tagacttact gttggaggtg cagaccaagg tgcctggcct   2460
ggctaatggt gtgaagtgtg gcagccccgg ccagctgcag ggccgtagca tcttcgcgca   2520
ggacctgcgg ctgtgcctgg atgaggtcct ctcttgggac tgctttggcc tttcactctt   2580
ggctgtggcc gtgggcatgg tggtgcctat actgcaccat ctctgcggct gggacgtctg   2640
gtactgtttt catctgtgcc tggcatggct acctttgctg gcccgcagcc gacgcagcgc   2700
ccaaactctc ccttatgatg ccttcgtggt gttcgataag gcacagagcg cagttgccga   2760
ctgggtgtat aacgagctgc gggtgcggct ggaggagcgg cgcggtcgcc gagccctacg   2820
cttgtgtctg gaggaccgag attgctgccc tggccagacg ctcttcgaga acctctgggc   2880
ttccatctat gggagccgca agactctatt tgtgctggcc cacacggacc gcgtcagtgg   2940
cctcctgcgc accagcttcc tgctggctca gcagcgcctg ttggaagacc gcaaggacgt   3000
ggtggtgttg gtgatcctgc gtccggatgc ccaccgctcc cgctatgtgc gactgcgcca   3060
gcgtctctgc cgccagagtg tgctcttcct gccccagcag cccaacgggc agggggctt    3120
ctgggcccag ctgagtacag ccctgactag ggacaaccgc cacttctata ccagaacttt   3180
ctgccgggga cctacagcag aatagctcag agcaacagct ggaaacagct gcatcttcat   3240
gcctggttcc cgagttgctc tgcctgcctt gctctgtctt actacaccgc tatttggcaa   3300
gtgcgcaata tatgctacca agccaccagg cccacggagc aaaggttggc agtaaagggt   3360
agtttttctt ccatgcatct ttcaggagag tgaagataga caccgaccc acacagaaca    3420
ggactggagt tcattctctg cccctccacc ccactttgcc tgtctctgta t            3471

<210> SEQ ID NO 41
<211> LENGTH: 4286
<212> TYPE: DNA
<213> ORGANISM: Mus musculus

<400> SEQUENCE: 41
ttgaaatctc acagcccggt tggttgcagt gacccacttc gttgaacata ttcttcctaa     60
tcctagtact ttcaatttgc tctattccct ggtgtctatg catttaaatc gactatgggg    120
ccattcttcc ttgaaccacc acagaagaca ttagctctct gggatccttg ttaatttttt    180
ctcctcttac atagcaccta cgcttggaac atatgccaga cacatctgtg agacacccct    240
tgccgctgca gctcatggat ggatgctgag ttcccccacg caccacactt cagcaggtgg    300
gtgtatttct gcttcacatt atactcccac acggccatgc atgtcaggca tggagcaggc    360
tcataaccca cttaattaag gtgatcatat cagatccttt atcaagatgc atagagtgct    420
cagtgcсctgt actatgatct cggatctttg ggagatgggc tagatagagt ctgggacaga   480
```

```
atacagcaga gaaaccgata tgtttattgt ccgatcatca gctaagcttc tgggagctag    540
gaatggggct ccttggatga acagaagtaa aaatgcctcg tctttatgac tttcaacttc    600
cctcagcagg tctggaatgg gtgaacaaac actgcctgcg tgggtgataa atagcctctt    660
tttgctgctt gtttgctgct tttatggttc tgggagggaa cctagaacct agcacatgct    720
agacaagtcc tctagcactg agctatctcc ccagcttgga tgaaatatct gtaaagtact    780
ggtgcccgtg tgtaaaatat gcaccattaa gtgttcaaga agaaaagact gggcatttct    840
gttccaccaa gacaagaaga atctgccagc agaatgtttg cgcagtcatt tgagcaaagg    900
ggtccaaggg acagtaccct ccagtgctgg ggacccatgt gccgagcctc aggctgtgat    960
gtggtgttgt ttttaattct ctcttttccc ataggatcat ggcatgtcaa cttgacttgc   1020
tcataggtgt gatcttcatg ccagccccg tgttggtaat atctccctgt tcttcagacg   1080
gcaggatagc cttttccga ggctgtaacc tcacccagat tccctggatc ctcaatacta   1140
ccactgagag gctcctgctc agcttcaact atatcagtat ggtggttgcc acatcatttc   1200
cactcctgga gcggctccag ttgctggagc tggggaccca gtatgctaac ttgaccattg   1260
gtccaggggc tttcagaaac ctgcccaatc ttaggatctt ggacttgggc caaagccaga   1320
tcgaagtctt gaatcgagat gcctttcaag gtctgcccca tctcttggaa cttcggctgt   1380
tttcctgtgg actctccagt gctgtgttaa gtgacggtta cttcagaaat ctatattcat   1440
tagctcgctt agacctatct ggcaaccaga ttcacagcct ccgcctccat tcttcattcc   1500
gggaactgaa ttccttaagc gacgtaaatt ttgctttcaa ccaaatattc actatatgtg   1560
aagatgaact cgagcctctg cagggcaaaa cactgtcttt ctttggcctc aaattaacta   1620
agctgttcag cagagtctct gtgggctggg agacatgcag gaaccccttc agaggcgtga   1680
ggctagaaac tctagatctt tctgaaaatg gctggacggt ggacatcaca aggaacttca   1740
gcaacatcat ccagggaagc cagatttcct cttttgattct taaacaccac atcatgggtc   1800
ctggctttgg cttccagaac atcagagatc ctgaccagag cacatttgcc agcctggcca   1860
gaagttcggt gctgcaactg gacctttcgc acggctttat cttctccttg aatcctcgac   1920
tgtttgggac actgaaggat ttgaagatgc tgaaccttgc cttcaacaag ataaacaaga   1980
ttggagagaa tgccttttat gggcttgaca gcctccaggt tctcaatcta cctataatc   2040 ttttggggga actctataat tccaacttct atgggcttcc tagagtagcc tacgttgacc   2100
ttcaaaggaa ccacattggg atcattcaag accaaacatt cagattatta aaaacgttac   2160
aaaccttaga tctccgtgac aatgctctta aggccattgg ttttattcca agcatacaga   2220
tggtcctcct gggaggcaat aagctggtcc atttgccaca catccacttt actgccaact   2280
tcctagagtt atctgaaaac aggctagaaa acctgtccga cctctacttc ctcctgcgag   2340
tcccccagct ccagtttctc atcttgaatc agaatcgcct ttcgtcatgc aaggcagccc   2400
acactccctc ggagaaccca agcttagaac agcttttcct tacagagaat atgctgcagc   2460
tggcctggga gaccggcctc tgttgggatg ttttcaagg cctttccgc ctccagattc    2520 tttacctgag taataactac cttaatttcc ttccacctgg gatatttaac gacctggttg   2580
cattacggat gcttagtctt agtgctaaca agctgaccgt gctctctccg ggcagtttac   2640
ctgctaattt agagattctc gacatatcta gaaatcagct tttgtgtcct gaccctgctt   2700 tgtttttcttc gcttcgtgtt ttggacataa ctcataacga gttcgtctgc aactgtgaac   2760
ttagcacttt tatctcctgg ctcaaccaaa ccaacgtcac cctgttcggc tctcctgcag   2820
acgtgtattg catgtaccct aactcactgc taggggggctc cctctacaac atatccaccg   2880
```

| | |
|---|---:|
| aagactgcga tgaagaggaa gccatgcggt ccctaaagtt ttcccttttc atcctgtgca | 2940 |
| cggtcacttt gactctattc ctcgtcatca cccttgtagt cataaagttc cggggaatct | 3000 |
| gtttcctgtg ctataagacc atccagaagc tggtgttcaa ggacaaggtc tggagtttgg | 3060 |
| aacctggtgc atatagatat gatgcctact tctgcttcag cagcaaagac tttgaatggg | 3120 |
| cacagaatgc tttgctcaaa cacctggatg ctcactacag ttcccgaaac aggctcaggc | 3180 |
| tatgctttga agaaagagac ttcattccgg gggaaaacca tatctccaac atccaggcgg | 3240 |
| ctgtctgggg cagcaggaag acggtgtgtc tagtgagcag acacttcctg aaggatggtt | 3300 |
| ggtgcctgga ggccttcagg tatgcccaga gccgagtct gtctgacctc aagagcattc | 3360 |
| tcatcgtggt ggtggtggga tcgctgtccc agtatcagct gatgagacat gagaccatca | 3420 |
| gagggtttct gcaaaagcaa cagtacttga gtggcctga agaccccag gatgttggct | 3480 |
| ggtttctcga taaactctcc ggatgcattc taaaggaaga aaaggaaag aaaagaagca | 3540 |
| gttccatcca gttgcgaacc atagcaacca tttcctagca ggagcgcctc ctagcagaag | 3600 |
| tgcaagcatc gtagataact ctccacgctt tatccgcaca gccgctgggg gtccttccct | 3660 |
| ggagtcattt ttctgacaat gaaaacaaca ccaatctctt gattttcat gtcaacaggg | 3720 |
| agctttgtct tcactgtttt ccaaatggaa agtaagaggt ccagaaagct gcctctaagg | 3780 |
| gctctcacct gccattgatg tccttcagg cccaatgaca tggtttccct ccatcctatt | 3840 |
| gcgtactgtc tgctacccag gtggcaagag caccttggga gaagttacag gcagcttcat | 3900 |
| gctttctgtg ctgttcagtt caaaagcagg tgccttgaga atcctgaatt caagcactct | 3960 |
| gtagaacatg gacagacaag atgggtcctt ctctggccat aggcatgagg gccagttgct | 4020 |
| gaggactgct ctcactacac ctaagtgcac aagtgataag aagttggaca gatagacaga | 4080 |
| tagcagcagt cccattgctg tagccagaat gcacttattt cctgttctga ccctgcaggc | 4140 |
| ccagcttttg ggaccacag ccatgttctg cacgggacct ctcaacctgg cattcatgcc | 4200 |
| cttcacgac ttagcaccgg cctgcccttc tttcttcccc acaactatac aagagctgtt | 4260 |
| gcaaccactg aaaaaaaaaa aaaaaa | 4286 |

<210> SEQ ID NO 42
<211> LENGTH: 605
<212> TYPE: DNA
<213> ORGANISM: Mus musculus

<400> SEQUENCE: 42

| | |
|---|---:|
| ggatccccgg gcagagctgg gggggatt gttagcatct cttgataaac ttaattgtct | 60 |
| ctcgtcactg acggcacaga gctattgatg ggtctcaacc cccagctagt tgtcatcctg | 120 |
| ctcttctttc tcgaatgtac caggagccat atccacggat gcgacaaaaa tcacttgaga | 180 |
| gagatcatcg gcattttgaa cgaggtcaca ggagaaggga cgccatgcac ggagatggat | 240 |
| gtgccaaacg tcctcacagc aacgaagaac accacagaga gtgagctcgt ctgtagggct | 300 |
| tccaaggtgc ttcgcatatt ttatttaaaa catgggaaaa ctccatgctt gaagaagaac | 360 |
| tctagtgttc tcatggagct gcagagactc tttcgggctt ttcgatgcct ggattcatcg | 420 |
| ataagctgca ccatgaatga gtccaagtcc acatcactga aagacttcct ggaaagccta | 480 |
| aagagcatca tgcaaatgga ttactcgtag tactgagcca ccatgcttta acttatgaat | 540 |
| ttttaatggt tttattttaa tatttatata tttataattc ataaaataaa atatttgtat | 600 |
| aatgt | 605 |

<210> SEQ ID NO 43

```
<211> LENGTH: 1087
<212> TYPE: DNA
<213> ORGANISM: Mus musculus

<400> SEQUENCE: 43
ccaagaacga tagtcaattc cagaaaccgc tatgaagttc ctctctgcaa gagacttcca      60
tccagttgcc ttcttgggac tgatgctggt gacaaccacg gccttcccta cttcacaagt     120
ccggagagga gacttcacag aggataccac tcccaacaga cctgtctata ccacttcaca     180
agtcggaggc ttaattacac atgttctctg ggaaatcgtg gaaatgagaa agagttgtg      240 caatggcaat tctgattgta tgaacaacga tgatgcactt gcagaaaaca atctgaaact     300
tccagagata caaagaaatg atggatgcta ccaaactgga tataatcagg aaatttgcct     360
attgaaaatt tcctctggtc ttctggagta ccatagctac ctggagtaca tgaagaacaa     420
cttaaaagat aacaagaaag acaaagccag agtccttcag agagatacag aaactctaat     480
tcatatcttc aaccaagagg taaagatttt acataaaata gtccttccta ccccaatttc     540
caatgctctc ctaacagata agctggagtc acagaaggag tggctaagga ccaagaccat     600
ccaattcatc ttgaaatcac ttgaagaatt tctaaaagtc actttgagat ctactcggca     660
aacctagtgc gttatgccta agcatatcag tttgtggaca ttcctcactg tggtcagaaa     720
atatatcctg ttgtcaggta tctgacttat gttgttctct acgaagaact gacaatatga     780
atgttgggac actattttaa ttatttttaa tttattgata atttaaataa gtaaacttta     840
agttaattta tgattgatat ttattatttt tatgaagtgt cacttgaaat gttatatgtt     900
atagttttga aatgataacc taaaaatcta tttgatataa atattctgtt acctagccag     960
atggtttctt ggaatgtata agtttacctc aatgaattgc taatttaaat atgttttttaa    1020 agaaatcttt gtgatgtatt tttataatgt ttagactgtc ttcaaacaaa taattatat    1080 tatattt                                                              1087

<210> SEQ ID NO 44
<211> LENGTH: 1345
<212> TYPE: DNA
<213> ORGANISM: Mus musculus

<400> SEQUENCE: 44
cgaggcctaa taggctcatc tgggatcctc tccagccaag cttccttgtg caagtgtctg      60
aagcagctat ggcaactgtt cctgaactca actgtgaaat gccaccttttt gacagtgatg     120 agaatgacct gttctttgaa gttgacggac cccaaaagat gaagggctgc ttccaaacct     180
ttgacctggg ctgtccagat gagagcatcc agcttcaaat ctcacagcag cacatcaaca     240
agagcttcag gcaggcagta tcactcattg tggctgtgga gaagctgtgg cagctacctg     300
tgtctttccc gtggaccttc caggatgagg acatgagcac cttcttttcc ttcatctttg     360
aagaagagcc catcctctgt gactcatggg atgatgatga taacctgctg gtgtgtgacg     420
ttcccattag acagctgcac tacaggctcc gagatgaaca acaaaaaagc ctcgtgctgt     480
cggacccata tgagctgaaa gctctccacc tcaatggaca gaatatcaac caacaagtga     540
tattctccat gagctttgta caaggagaac caagcaacga caaaatacct gtggccttgg     600
gcctcaaagg aaagaatcta tacctgtcct gtgtaatgaa agacggcaca cccaccctgc     660
agctggagag tgtggatccc aagcaatacc caaagaagaa gatggaaaag cggtttgtct     720
tcaacaagat agaagtcaag agcaaagtgg agtttgagtc tgcagagttc cccaactggt     780
acatcagcac ctcacaagca gagcacaagc ctgtcttcct gggaaacaac agtggtcagg     840
```

| | | |
|---|---|---|
| acataattga cttcaccatg gaatctgtgt cttcctaaag tatgggctgg actgtttcta | 900 |
| atgccttccc cagggcatgt gaaggagctc ccttgtcatg aatgagcaga cagctcaatc | 960 |
| tctaggagac tccttagtcc tcggccaaga caggtcgctc agggtcacaa gaaaccatgg | 1020 |
| cacattctgt tcaaagagag cctgtgtttt cctccttgcc tctgatgggc aaccacttac | 1080 |
| ctatttattt atgtatttat tgattggttg atctatttaa gttgattcaa ggggacatta | 1140 |
| ggcagcactc tctagaacag aacctagctg tcaacgtgtg ggggatgaat tggtcatagc | 1200 |
| ctgcactgag gtctttcatt gaagctgaga ataaataggt tcctataata tggatgagaa | 1260 |
| tttttatgaa tgaagcacca gcacattgct ttgatgagta tgaaataaat ttcattaaaa | 1320 |
| caaacaaaaa aaaaaaaaaa aaaaa | 1345 |

<210> SEQ ID NO 45
<211> LENGTH: 1209
<212> TYPE: DNA
<213> ORGANISM: Mus musculus

<400> SEQUENCE: 45

| | | |
|---|---|---|
| atatagctgc catcggctga cctagagaag cacatcagc tgatcctttg gaccctctga | 60 |
| cttgagacag aagttctggg cttctcctcc tgcggcctag ctctgagaca atgaacgcta | 120 |
| cacactgcat cttggctttg cagctcttcc tcatggctgt ttctggctgt tactgccacg | 180 |
| gcacagtcat tgaaagccta gaaagtctga ataactattt taactcaagt ggcatagatg | 240 |
| tggaagaaaa gagtctcttc ttggatatct ggaggaactg gcaaaaggat ggtgacatga | 300 |
| aaatcctgca gagccagatt atctctttct acctcagact ctttgaagtc ttgaaagaca | 360 |
| atcaggccat cagcaacaac ataagcgtca ttgaatcaca cctgattact accttcttca | 420 |
| gcaacagcaa ggcgaaaaag gatgcattca tgagtattgc caagtttgag gtcaacaacc | 480 |
| cacaggtcca gcgccaagca ttcaatgagc tcatccgagt ggtccaccag ctgttgccgg | 540 |
| aatccagcct caggaagcgg aaaaggagtc gctgctgatt cggggtgggg aagagattgt | 600 |
| cccaataaga ataattctgc cagcactatt tgaattttta aatctaaacc tatttattaa | 660 |
| tatttaaaac tatttatatg gagaatctat tttagatgca tcaaccaaag aagtatttat | 720 |
| agtaacaact tatatgtgat aagagtgaat tcctattaat atatgtgtta tttataattt | 780 |
| ctgtctcctc aactatttct ctttgaccaa ttaattattc tttctgacta attagccaag | 840 |
| actgtgattg cggggttgta tctgggggtg ggggacagcc aagcggctga ctgaactcag | 900 |
| attgtagctt gtacctttac ttcactgacc aataagaaac attcagagct gcagtgaccc | 960 |
| cgggaagtgc tgctgatggg aggagatgtc tacactccgg gccagcgctt taacagcagg | 1020 |
| ccagacagca ctcgaatgtg tcaggtagta acaggctgtc cctgaaagaa agcagtgtct | 1080 |
| caagagactt gacacctggt gcttccctat acagctgaaa actgtgacta cacccgaatg | 1140 |
| acaaataact cgctcatttta tagtttatca ctgtctaatt gcatatgaat aaagtatacc | 1200 |
| tttgcaacc | 1209 |

<210> SEQ ID NO 46
<211> LENGTH: 2094
<212> TYPE: DNA
<213> ORGANISM: Mus musculus

<400> SEQUENCE: 46

| | | |
|---|---|---|
| cgccgccgcc gccgcccttc gcgcccagg ccgtccccct cctcctcccg ccgcggatcc | 60 |
| tccagacagc caggccccg gccggggcag gggggacgcc ccttcggggc accccggct | 120 |

-continued

```
ctgagccgca ctcggagtcg gcctccgctg ggagccggca aaggagcagc cgaggagccg      180
tccgaggccc cagagtctga gaccagccgc cgccgcaggg aggaggggga ggaggagtgg      240
gaggagggac gagctggttg agagaagagg aaaaaagttt tgagacttt ccgctgctac      300 tgcaagtcag agacgtgggg acttcttggc actgcgctgt ctcgcaagga ggcaggacct      360
gaggactcca gacagccctg ctcaccgtcg tggacactcg atcgctaccc ggcgttcctc      420
agacgcccct attccggacc agccctcggg agccacaaac cccgcctccc gcgaagactt      480
caccccaaag ctgggcgca cccttgcac gccgccctcc cccagcctg cctcttgagt      540 ccctcgcatc ccaggaccct ctctcccccg agaggcagat ctccctcgga cctgctggca      600
gtagctcccc tatttaagaa cacccacttt tggatctcag agagcgctca tctcgatttt      660
taccctggtg gtatactgag acaccttggt gtcagagcct caccgcgact cctgctgctt      720
tctccctcaa cctcaaatta ttcaggacta tcacctacct ttccttggga gaccccaccc      780
cacaagccct gcagggggcgg ggcctccgca tcccacctt gccgagggtt cccgctctcc      840
gaagtgccgt ggggcgccgc ctcccccatg ccgccctcgg ggctgcggct actgccgctt      900
ctgctcccac tcccgtggct tctagtgctg acgcccggga ggccagccgc gggactctcc      960
acctgcaaga ccatcgacat ggagctggtg aaacggaagc gcatcgaagc catccgtggc      1020
cagatcctgt ccaaactaag gctcgccagt ccccaagcc aggggaggt accgcccggc      1080 ccgctgcccg aggcggtgct cgctttgtac aacagcaccc gcgaccgggt ggcaggcgag      1140
agcgccgacc cagagccgga gcccgaagcg gactactatg ctaaagaggt cacccgcgtg      1200
ctaatggtgg accgcaacaa cgccatctat gagaaaacca agacatctc acacagtata      1260 tatatgttct tcaatacgtc agacattcgg gaagcagtgc ccgaaccccc attgctgtcc      1320
cgtgcagagc tgcgcttgca gagattaaaa tcaagtgtgg agcaacatgt ggaactctac      1380
cagaaatata gcaacaattc ctggcgttac cttggtaacc ggctgctgac ccccactgat      1440
acgcctgagt ggctgtcttt tgacgtcact ggagttgtac ggcagtggct gaaccaagga      1500
gacggaatac agggctttcg attcagcgct cactgctctt gtgacagcaa agataacaaa      1560
ctccacgtgg aaatcaacgg gatcagcccc aaacgtcggg gcgacctggg caccatccat      1620
gacatgaacc ggccccttcct gctcctcatg ccaccccccc tggaaagggc ccagcacctg      1680
cacagctcac ggcaccggag agccctggat accaactatt gcttcagctc cacagagaag      1740
aactgctgtg tgcggcagct gtacattgac tttaggaagg acctgggttg gaagtggatc      1800
cacgagccca agggctacca tgccaacttc tgtctgggac cctgcccta tatttggagc      1860 ctggacacac agtacagcaa ggtccttgcc ctctacaacc aacacaaccc gggcgcttcg      1920
gcgtcaccgt gctgcgtgcc gcaggctttg gagccactgc catcgtcta ctacgtgggt      1980 cgcaagccca aggtggagca gttgtccaac atgattgtgc gctcctgcaa gtgcagctga      2040
agccccgccc cgccccgccc ctcccggcag gcccggcccc gccccgccc cgcc           2094
```

<210> SEQ ID NO 47
<211> LENGTH: 939
<212> TYPE: DNA
<213> ORGANISM: Mus musculus

<400> SEQUENCE: 47

```
atcacccttg ctaatcactc ctcacagtga cctcaagtcc tgcaggcatg tacagcatgc      60
agctcgcatc ctgtgtcaca ttgacacttg tgctccttgt caacagcgca cccacttcaa      120
gctccacttc aagctctaca gcggaagcac agcagcagca gcagcagcag cagcagcagc      180
```

-continued

```
agcagcacct ggagcagctg ttgatggacc tacaggagct cctgagcagg atggagaatt    240
acaggaacct gaaactcccc aggatgctca ccttcaaatt ttacttgccc aagcaggcca    300
cagaattgaa agatcttcag tgcctagaag atgaacttgg acctctgcgg catgttctgg    360
atttgactca aagcaaaagc tttcaattgg aagatgctga gaatttcatc agcaatatca    420
gagtaactgt tgtaaaacta aagggctctg acaacacatt tgagtgccaa ttcgatgatg    480
agtcagcaac tgtggtggac tttctgagga gatggatagc cttctgtcaa agcatcatct    540
caacaagccc tcaataacta tgtacctcct gcttacaaca cataaggctc tctatttatt    600
taaatattta actttaattt attttttggat gtattgttta ctatcttttg taactactag    660
tcttcagatg ataaatatgg atctttaaag attcttttg taagccccaa gggctcaaaa    720
atgttttaaa ctatttatct gaaattattt attatattga attgttaaat atcatgtgta    780
ggtagactca ttaataaaag tatttagatg attcaaatat aaataagctc agatgtctgt    840
catttttagg acagcacaaa gtaagcgcta aaataacttc tcagttattc ctgtgaactc    900
tatgttaatc agtgttttca agaaataaag ctctcctct                           939
```

<210> SEQ ID NO 48
<211> LENGTH: 20
<212> TYPE: PRT
<213> ORGANISM: Mus musculus

<400> SEQUENCE: 48

```
Gly Pro Thr His Leu Phe Gln Pro Ser Leu Val Leu Asp Met Ala Lys
1               5                   10                  15

Val Leu Leu Asp
            20
```